(12) United States Patent
LeBlanc et al.

(10) Patent No.: US 11,105,814 B2
(45) Date of Patent: Aug. 31, 2021

(54) ASSAY FOR QUANTITATION OF PROTEINS AND PEPTIDES USING STABLE ISOTOPE STANDARDS

(71) Applicant: UVic Industry Partnerships Inc., Victoria (CA)

(72) Inventors: Andre Marc Joseph LeBlanc, Montreal (CA); Derek Scott Smith, Victoria (CA)

(73) Assignee: UVic Industry Partnerships Inc., Victoria (CA)

(*) Notice: Subject to any disclaimer, the term of this patent is extended or adjusted under 35 U.S.C. 154(b) by 228 days.

(21) Appl. No.: 16/307,911

(22) PCT Filed: Apr. 7, 2017

(86) PCT No.: PCT/IB2017/052029
§ 371 (c)(1),
(2) Date: Dec. 6, 2018

(87) PCT Pub. No.: WO2017/212348
PCT Pub. Date: Dec. 14, 2017

(65) Prior Publication Data
US 2019/0187151 A1 Jun. 20, 2019

Related U.S. Application Data

(60) Provisional application No. 62/346,246, filed on Jun. 6, 2016.

(51) Int. Cl.
*G01N 33/68* (2006.01)
*G01N 33/48* (2006.01)
(Continued)

(52) U.S. Cl.
CPC ........ *G01N 33/6848* (2013.01); *G01N 33/48* (2013.01); *G01N 33/574* (2013.01);
(Continued)

(58) Field of Classification Search
None
See application file for complete search history.

(56) References Cited

U.S. PATENT DOCUMENTS

| 7,759,130 B2 | 7/2010 | Oda et al. |
| 2004/0214338 A1 | 10/2004 | Borchers |

(Continued)

FOREIGN PATENT DOCUMENTS

| WO | WO 2004/031730 A2 | 4/2004 |
| WO | WO 2008/013530 A1 | 1/2008 |
| WO | WO 2011/116028 A1 | 3/2011 |

OTHER PUBLICATIONS

Samuelsson, L.B., et al. Validation of biomarkers of CVD risk from dried blood spots in community-based research: Methodologies and study-specific serum equivalencies, Biodemography Soc. Biol. 2015, 61(3): 285-297 (Year: 2015).*

(Continued)

*Primary Examiner* — Xiaoyun R Xu
(74) *Attorney, Agent, or Firm* — Klarquist Sparkman, LLP

(57) ABSTRACT

A methodology for the precise calibration of molecule quantifying assays is disclosed. The method uses stable isotope labeled molecules with distinguishable masses to act as internal and calibration standards that are free from endogenous interference. Furthermore, stable isotope labeled molecules allows for calibration within a test matrix. In some examples, stable isotope labeled peptides are used as internal and calibration standards for mass spectrometry assays for quantification of peptide biomarkers.

20 Claims, 6 Drawing Sheets

Specification includes a Sequence Listing.

SIS 1: For calibration standards and QCs
SIS 2: Internal standard (equal in all sample types)

Free of interference from endogenous peptide in any human plasma

(51) Int. Cl.
*G01N 33/574* (2006.01)
*G01N 33/60* (2006.01)
(52) U.S. Cl.
CPC ......... *G01N 33/60* (2013.01); *G01N 2560/00* (2013.01); *G01N 2800/32* (2013.01); *G01N 2800/50* (2013.01)

(56) References Cited

U.S. PATENT DOCUMENTS

2012/0015371 A1 1/2012 West et al.
2015/0219666 A1 8/2015 Li et al.

OTHER PUBLICATIONS

International Search Report and Written Opinion dated Jun. 29, 2017, by the CA Intellectual Property Office acting as ISA for application No. PCT/IB2017/052029, 8 pages.
LeBlanc, et al. "Highly multiplexed MRM-based peptide quantitation in human plasma using two different stable isotope labeled peptides for calibration." Poster presented at 64th annual ASMS conference on Jun. 5-9, 2016, in San Antonio, TX, 1 page.
LeBlanc, et al. "Highly multiplexed MRM-based peptide quantitation in human plasma using two different stable isotope labeled peptides for calibration." Poster presented at 8th Annual CNPN Symposium on Apr. 12-13, 2016, in Montreal, QC, 7 pages.
Mani, et al. "Statistical characterization of multiple-reaction monitoring mass spectrometry (MRM-MS) assays for quantitative proteomics." *BMC Bioinformatics*, vol. 13, No. 16: pp. S9 (2012).
Percy, et al. "Standardized protocols for quality control of MRM-based plasma proteomic workflows." *Journal of Proteome Research*, vol. 12, No. 1, pp. 222-233 (2012).
Wang, et al. "A new calibration curve calculation method for absolute quantification of drug metabolizing enzymes in human liver microsomes by stable isotope dilution mass spectrometry." *Analytical Methods*, vol. 7, No. 14, pp. 5934-5941 (2015).
LeBlanc et al., "Highly Multiplexed MRM-based Peptide Quantitation in Human Plasma Using Two Different Stable Isotope Labeled Peptides for Calibration," Abstract published for 64th ASMS Conference on Mass Spectrometry and Allied Topics, held Jun. 5-9, 2016, San Antonio, Texas (2 pages).
Mayya and Han, "Proteomic applications of protein quantification by isotope-dilution mass spectrometry," *Expert Review of Proteomics*, vol. 3, No. 6, pp. 597-610 (2006).

* cited by examiner

ASSAY FOR QUANTITATION OF PROTEINS AND PEPTIDES USING STABLE ISOTOPE STANDARDS

CROSS REFERENCE TO RELATED APPLICATIONS

This is the U.S. National Stage of International Application No. PCT/IB2017/052029, filed Apr. 7, 2017, which was published in English under PCT Article 21(2), which in turn claims the benefit of U.S. Provisional Application No. 62/346,246, filed Jun. 6, 2016. The provisional application is incorporated by reference herein in its entirety.

FIELD

This application relates to methods of quantifying molecules in a sample, such as a sample that includes a plurality of biomolecules. The methods allow for calibration in a test matrix, free from endogenous interference.

BACKGROUND

Quantification of target molecules in a complex sample can require precise instrument calibration and uniform standards. In some cases, calibration is performed in an identical matrix to that of a test sample. For targeted protein quantitation, several unique challenges make this strategy difficult to achieve, especially for highly multiplexed assays of endogenous protein panels. For this application, the chosen surrogate stable isotope labelled standard (SIS) peptide or peptides (including winged peptides) for each protein in the assay is most commonly the choice for calibration standard, since whole protein and concatenated peptide standards are normally too time consuming and/or costly to produce on a large scale despite evidence that these types of standards can improve quantitation through better correction of the digestion step [10-14]. However, even with a protein standard, the digestion of concatenated peptides can be different than in a native protein since the digestion is affected by post-translational modifications (PTMs) and protein structure, which may be different between the two. The use of peptide standards for these applications implies that large-scale multiplexed assays often need to rely on empirically verified sample preparation methods to assure, as much as possible, the most complete and reproducible protein extraction and digestion protocol for a multitude of different proteins at once. This means that sample processing up to the digestion step is somewhat decoupled from the analytical performance of the assay, since the standards (and internal standards) are normally added after completion of the digestion step. The assay is thus actually the quantitation of surrogate peptide present in digested samples, as opposed to quantitation of protein in the original untreated sample.

Several factors can cause the measured surrogate peptide concentration not to reflect the actual protein concentration, such as inefficient digestion, modifications to the peptide of interest either in vivo or during sample preparation, or even peptide adsorption to plastics during preparation and peptide handling.[15] Despite these issues, these assays can be reproducible between laboratories and perform well for their intended purposes.[16, 17] For these reasons, however, it is not feasible to determine the absolute accuracy (of protein concentration), which would be the ideal analytical figure of merit for highly multiplexed protein assays using a bottom-up approach. This, however, should not mean that the accuracy of the surrogate peptide measurement should not be determined as a measure of the assay performance. Nonetheless, even the most recent guidelines and best practices for assay validation[18] do not include criteria to directly monitor the accuracy of assays, which can be viewed as a problem for proper assay standardization and validation within the field.

In the case of highly multiplexed endogenous protein quantitation in biofluids, such as human plasma, the major hurdle in implementing both the ideal calibration strategy and determining the assay's accuracy is the lack of blank matrix. When measuring large panels of protein in plasma, the unknown endogenous levels of the target analytes in pooled matrix prevent the implementation of ideal calibration curve strategies since they are always present at varying concentrations and interfere with quantitation of the (unlabeled) surrogate peptides. Consequently, several alternative calibration strategies are employed by different laboratories. These strategies include generating "reverse" standard curves (where endogenous and/or light peptides are used to normalize the responses of the SIS standards while the heavy (SIS) peptides are used to normalize unknown samples), using surrogate matrices (such as buffer containing albumin) for preparing standards or single-point measurements (i.e., spiking a known amount of isotope labeled peptide in the unknown sample).

Precise and robust quantitation of the endogenous plasma proteome by mass spectrometry (MS)-based methods is required for biomedical research and clinical applications.[1-3] The main advantages of MS-based methods compared to traditional protein quantitation using immuno-based methods include increased specificity and high multiplexing capacity.[4] Furthermore, antibody development can be costly and the resultant antibodies of varied quality and antibody-based assays are not reliably quantitative. The strategy most suitable for achieving these highly multiplexed assays is a targeted bottom-up approach consisting of digesting the protein sample and monitoring specific unique peptides generated from each protein of interest by tandem mass spectrometry. There has been a movement towards standardizing targeted protein quantification across the community,[5] since it is generally recognized that to achieve its potential, targeted bottom-up strategies must be made more rigorous.

The choice of calibration strategies can greatly affect the performance protein quantitation assays.[6] The best calibration strategy for MS-based quantitation, regardless of the nature of the analyte, involves an external calibration curve prepared in a blank matrix where the standard compound is identical to the analyte and a stable isotope labeled standard (SIS) version of the analyte is used as the internal standard. The internal standard is added to all samples (unknowns and standards) in order to normalize and correct for variations in analyte response. The SIS standard is added as early as possible during sample processing and therefore also compensates for any loses prior to analysis.[7] This method is considered to be the "gold standard" and has been followed for years in regulated bioanalysis,[8, 9] particularly for small exogenous molecules such as drugs.

Precise and accurate quantitation of the endogenous plasma proteome is a requirement for fundamental and biomedical research as well as for clinical applications. Targeted detection of peptides in a bottom-up strategy is the most common and precise mass spectrometry-based quantitation approach when combined with the use of stable isotope labeled peptides. However, when measuring protein in plasma, the unknown endogenous levels prevent the implementation of best calibration strategies since no blank matrix is available. Consequently, several alternative calibration strategies are employed by different laboratories. There is a need for calibration strategies with increased accuracy and conformity with recommended guidelines (e.g., as set by the FDA guidelines for bioanalytical method validation[8].)

SUMMARY

The present application discloses methods of quantifying one or more target molecules in a test sample. In one example, the methods include the use of two different or distinguishable stable isotope labeled standard (SIS) molecules, or isotopologues. The first and second stable isotope labeled molecules have distinguishable masses. The first stable isotope labeled molecule is added to a control sample in two or more different concentrations. The second stable isotope labeled molecule is added to the control samples and to the test sample at a constant (e.g., the same) concentration. An instrument signal magnitude is detected or measured from the target molecule (for example in the test sample, control sample, or both), the first stable isotope labeled molecule (for example in the test sample, control sample, or both) and the second stable isotope labeled molecule (for example in both the in the test sample and the control sample). From the control sample, a ratio is generated of the instrument signal magnitude for each different concentration of the first stable isotope labeled molecule to the instrument signal magnitude of the second stable isotope labeled molecule. A calibration curve can be generated using these ratios and the known concentration of the second stable isotope labeled molecules. Another ratio is generated of the instrument signal magnitude of the target molecule in the test sample to the instrument signal magnitude of the second stable isotope labeled molecule in the test sample. Plotting the ratio of the target molecule instrument signal magnitude to the second stable isotope labeled molecule instrument signal magnitude onto the generated calibration curve allows for the calculation of the concentration of the target molecule in the test sample.

In examples, the test sample can be any biological or environmental sample, such as a biofluid (such as blood plasma, dried blood spot, or urine), a tissue sample, or a food sample. The first and second stable isotope labelled molecules can be present in the test sample in their unlabeled (e.g., natural or native) forms.

In examples, the first and second stable isotope labelled molecules and the target molecule can be a biomarker, such as a nucleic acid molecule, protein, peptide, lipid, hormone, or metabolite. In some examples, the first and second stable isotope labelled molecules and the target molecule can be drugs or small molecules. The first and second stable isotope labelled molecules and the target molecule can have a mass-to-charge ratio with a positive mode m/z range of 1 to 3000, such as 1 to 2000, or 100 to 1000, or a negative mode m/z range of −3000 to −1, such as −2000 to −1, or −1000 to −100. Exemplary stable isotope labels that can be used include $^2H$, $^{13}C$, $^{15}N$, $^{18}O$, $^{34}S$ or a combination thereof.

In one example, the first and second stable isotope labeled molecules are tryptic peptides and are labelled at a lysine or arginine, such as a c-terminal lysine or arginine. In another example, the first or second stable isotope labeled molecules are peptides and are labelled at a phenylalanine or leucine, such as an internal phenylalanine or leucine, and in some example as at the C-terminus, such as a C-terminal Lys or Arg.

The methods of the present application be used in diagnosing or determining a risk of developing a disease. Exemplary diseases include cancer or cardiovascular disease. In some examples, the cancer is a cancer of the lung, breast, prostate, colon, kidney, pancreas, ovary, or brain.

In an example method, the two or more different concentrations of the first stable isotope labeled molecule span a suspected concentration of the target molecule present in the test sample.

In further examples of the methods, the instrument signal magnitude can be intensity, counts, or area under a curve. In one example, the instrument signal magnitude is an area under a curve determined by mass spectrometry.

In one example, the methods of the present application are useful for quantifying one or more target peptides in a test sample, such as a blood plasma sample. The method can include adding a first stable isotope labeled peptide to a control sample at two or more different concentrations and adding a second stable isotope labeled peptide to the control sample and to the test sample in a constant concentration. The label of the first and second stable isotope labeled peptides are different such that the first stable isotope labeled peptide and the second stable isotope labeled peptide have distinguishable masses. The method further includes detecting an area under a curve by mass spectrometry of the first stable isotope labeled peptide, the second stable isotope labeled peptide, and the target peptide. Using these areas under the curve, a ratio of the peak area (area under the curve) of each different concentration of the first stable isotope labeled peptide in the control sample to the peak area (area under the curve) of the second stable isotope labeled peptide in the control sample can be generated, thereby generating a calibration curve. Another ratio is generated of the peak area (area under the curve) of the target peptide in the test sample to the peak (area under the curve) of the second stable isotope labeled peptide in the test sample. The target peptide can be quantified by plotting the ratio of the peak area (area under the curve) of the target peptide to the peak area (area under the curve) of the second stable isotope labeled peptide in the test sample on the calibration curve. In one example, the peptides are tryptic peptides.

The foregoing and other objects and features of the disclosure will become more apparent from the following detailed description, which proceeds with reference to the accompanying figures.

SEQUENCE LISTING

Figure 1:
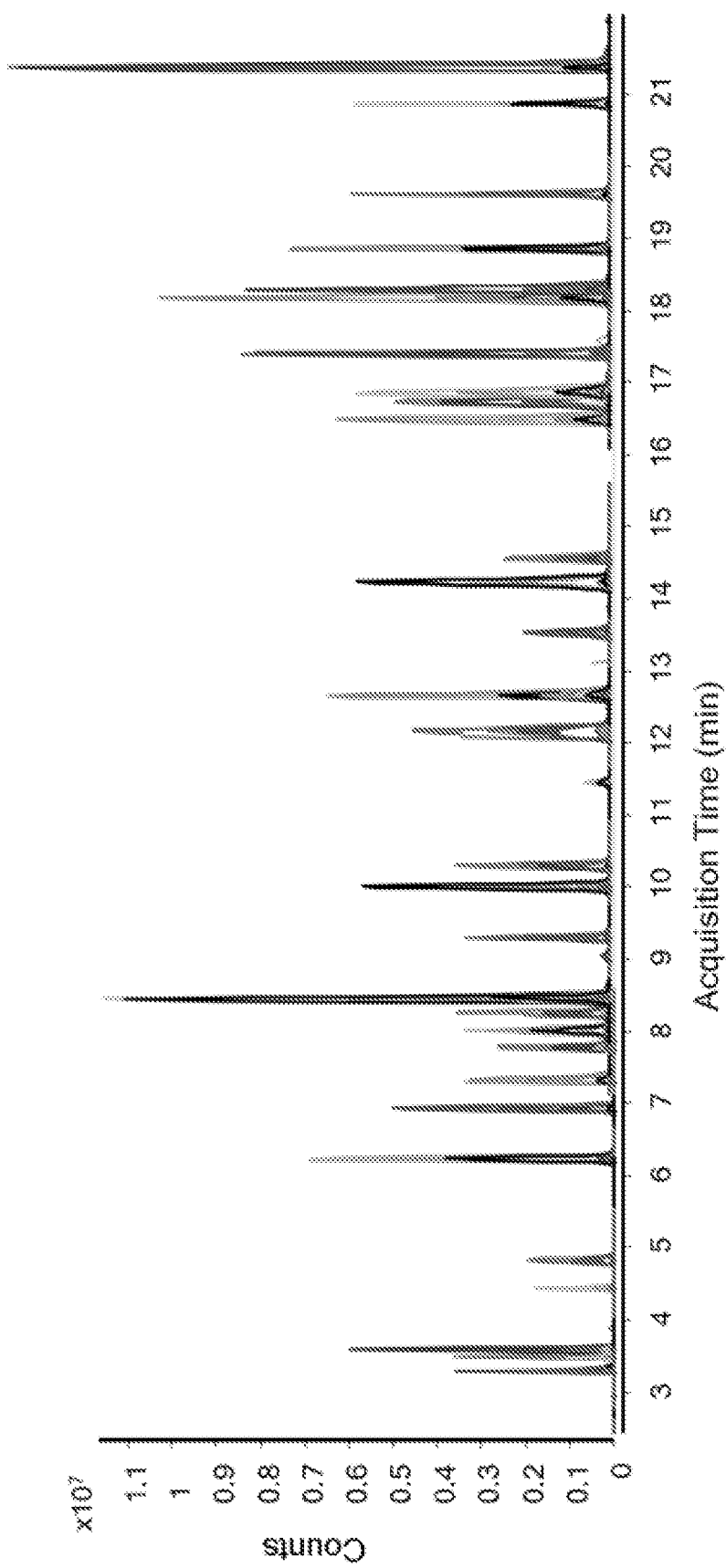
FIG. 1 is a graph showing the overlaid extracted ion chromatograms of all transitions (5 per peptide, per isotope) in a standard sample prepared in human plasma, showing the spread of retention times and relative concentration ranges.

The amino acid sequences listed in the accompanying sequence listing are shown using standard abbreviations for amino acids as defined in 37 C.F.R. 1.822. The sequence listing entitled SEQ Listing_ST25, generated on Nov. 27, 2018, is filed herewith and incorporated by reference.

SEQ ID NO: 1 is a tryptic peptide from L-selectin
SEQ ID NO: 2 is a tryptic peptide from Apolipoprotein M
SEQ ID NO: 3 is a tryptic peptide from Mannan-binding lectin serine protease 2
SEQ ID NO: 4 is a tryptic peptide from Peroxiredoxin-2
SEQ ID NO: 5 is a tryptic peptide from Collagen alpha-1(XVIII) chain
SEQ ID NO: 6 is a tryptic peptide from Xaa-Pro dipeptidase
SEQ ID NO: 7 is a tryptic peptide from Serotransferrin
SEQ ID NO: 8 is a tryptic peptide from Serotransferrin
SEQ ID NO: 9 is a tryptic peptide from C-reactive protein
SEQ ID NO: 10 is a tryptic peptide from Protein AMBP
SEQ ID NO: 11 is a tryptic peptide from Insulin-like growth factor-binding protein 3
SEQ ID NO: 12 is a tryptic peptide from Cartilage acidic protein 1
SEQ ID NO: 13 is a tryptic peptide from Alpha-1B-glycoprotein
SEQ ID NO: 14 is a tryptic peptide from Corticosteroid-binding globulin
SEQ ID NO: 15 is a tryptic peptide from Galectin-3
SEQ ID NO: 16 is a tryptic peptide from Myeloperoxidase
SEQ ID NO: 17 is a tryptic peptide from Lipopolysaccharide-binding protein
SEQ ID NO: 18 is a tryptic peptide from CD5 antigen-like
SEQ ID NO: 19 is a tryptic peptide from Hemopexin
SEQ ID NO: 20 is a tryptic peptide from Coagulation factor IX
SEQ ID NO: 21 is a tryptic peptide from Gelsolin
SEQ ID NO: 22 is a tryptic peptide from Apolipoprotein B-100
SEQ ID NO: 23 is a tryptic peptide from Coagulation factor X
SEQ ID NO: 24 is a tryptic peptide from Endothelial protein C receptor
SEQ ID NO: 25 is a tryptic peptide from Heparin cofactor 2
SEQ ID NO: 26 is a tryptic peptide from Antithrombin-III
SEQ ID NO: 27 is a tryptic peptide from Kininogen-1
SEQ ID NO: 28 is a tryptic peptide from Apolipoprotein L1
SEQ ID NO: 29 is a tryptic peptide from Complement component C9
SEQ ID NO: 30 is a tryptic peptide from Hyaluronan-binding protein 2
SEQ ID NO: 31 is a tryptic peptide from Vitamin K-dependent protein S
SEQ ID NO: 32 is a peptide derived from fibronectin

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2nd ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, Using *Antibodies: A Laboratory Manual*, Cold Spring Harbor Laboratory Press, 1999.

All publications, patent applications, patents, and other references mentioned herein are incorporated by reference in their entirety for all purposes. All sequences associated with the GenBank Accession numbers mentioned herein are incorporated by reference in their entirety as were present on Mar. 17, 2017, to the extent permissible by applicable rules and/or law.

In order to facilitate review of the various embodiments of the disclosure, the following explanations of specific terms are provided:

Biomarkers are measurable indices of biological functioning. Includes any substance, structure, or process that can be measured in the body or its products and influence or predict the incidence of outcome or disease. Biomarkers can be indicative of disease, such as infection, cancer, cardiovascular disease, metabolic functioning, toxicity, etc. Biomarkers may be protein, peptide, RNA (such as mRNA, miRNA), DNA (such as cDNA), small molecules, lipids, vitamins, hormones, metabolites, environmental toxins, antibodies or other quantifiable molecule within an organism. In one example, a biomarker is a target molecule.

Calibration Curve: A best fit curve for a graph or plot used to calibrate an instrument to a particular sample set. Calibration curves utilize multiple known concentrations of a standard (such as a stable isotope labeled molecule) to calibrate an instrument response. This labeled standard used in various concentrations may be referred to as a calibration standard. Utilizing a calibration curve, an unknown concentration can be derived from an assessed instrument signal. This instrument signal may be a ratio of the calibration standards to a known constant amount, e.g., the instrument signal of an internal standard. In one example a calibration curve is generated from data points plotting a ratio of instrument signal magnitudes of a calibration standard to an internal standard against the known concentration calibration standard.

Control Sample(s): A material used in an assay to allow for evaluation of the accuracy of an analytic method, such as mass spectrometry. A control sample is distinct from that desired to be analyzed (i.e., the test sample). In some examples, a control sample includes the same matrix as the test sample; for example if the test sample is blood plasma, the control sample may include normal human pooled blood plasma from non-test subjects. In other example, a control sample includes a different matrix as the test sample; for example if the test sample is blood plasma, the control sample may include PBS or other buffer. Control samples may contain known concentrations of labeled molecules, for example a standard isotope labelled calibration standard and a standard isotope labeled internal standard. These known concentrations can be used to create a calibration curve. Distinct from calibration, additional control samples may be used in quality control. In an example, quality control samples can also include a test matrix identical to the test matrix of the test sample and known concentrations of stable isotope labelled molecules.

Detect: To determine if a particular agent (such as one or more target molecules) is present or absent, and in some example further includes quantification of the agent if detected. In specific examples, detection is assessed in counts, intensity, or area under a curve. In an example, detection is by mass spectrometry.

Distinguishable mass: Distinct molecular and atomic masses, which can be distinguished by mass spectrometry. Different types of mass spectrometry differ in their sensitivity and identifiable mass ranges. The present methods utilize two stable isotope labelled molecules having distinguishable masses. Thus, the masses of the stable isotope labeled molecules used can be selected based on the particular mass spectrometry method used to distinguish them, such that the two stable isotope labeled molecules have masses that are different enough to be detected by the particular detection method used. This difference in masses can be accomplished by labeling a target molecule with different stable isotopes, or differing numbers of the same stable isotopes, or both, such that the resulting two stable isotope labeled target molecules are distinguishable from one another.

Internal Standard: A molecule within an assay having a constant value within a sample, which can be used as a benchmark. The internal standard can be endogenous or exogenous to the sample. In an example, an added stable isotope labeled molecule serves as an internal standard. In an example, the standard isotope labeled molecule is present in a test sample in its unlabeled form. An internal standard can be used in a uniform concentration in control and test samples. In an example, the control samples include calibration samples and quality control samples, both having the same, known and uniform concentration of internal standard.

Isotopes: Variants of a chemical element that differ in their number of neutrons. The number of protons is constant for a given element. The mass number of an isotope is its numbers of neutrons plus protons. For example, $^{12}C$, $^{13}C$, and $^{14}C$ are all isotopes of carbon having 6, 7 and 8 respective neutrons. Some isotopes are radioactive and subject to decay at regular intervals. Stable Isotopes are non-radioactive isotopes. They can be used as labels as they can be distinguished by mass from more common isotopes (e.g., isotopes of greater natural abundance). Example stable isotopes which can be used to stably label a molecule include $^{2}H$, $^{13}C$, $^{18}O$, and $^{34}S$.

Isotopologues: Molecules that differ only in their isotopic composition. Isotopologues can be distinguished by mass spectrometry. Distinct isotopologues can be used in labelling of molecules to distinguish them during mass spectrometry.

Mammal: This term includes both human and non-human mammals (such as primates). Similarly, the term "subject" includes both human and veterinary subjects (such as cats, dogs, cows, and pigs) and rodents (such as mice and rats).

Mass spectrometry: A technique used to assess the mass and charge of molecules. A mass spectrometer manipulates ions with electrical and magnetic fields allowing for sorting and separation of molecules according to mass and charge. Typically, mass spectrometry can assess molecules with a mass-to-charge ratio (M/z) of about 1-3,000 M/z. Since molecules are separated by mass, the presence of isotopes can be readily distinguished. Example isotopes for use with mass spectrometry include $^{2}H$, $^{13}C$, and $^{15}N$, $^{18}O$ and $^{34}S$.

Multiple Reaction Monitoring (MRM): A targeted assay using mass spectrometry. MRM allows for targeted quantification of proteins or peptides within a sample, such as a biological or environmental sample, such as samples that include a plurality of different molecules. The targeted approach allows for greater speed, accuracy and sensitivity than quantification of all molecules within a sample.

Serial Dilution: A stepwise dilution, typically with a constant dilution factor. Commonly, though not necessarily, serial dilutions have a dilution factor of 10, resulting in a logarithmic array of concentrations. For example, 1M, 01.M, 0.01M, 0.001M, etc. . . . . .

Stable Isotope Labelled Molecule: A molecule that includes or contains one or more stable isotopes (such as 1, 2, 3, 4 or 5 stable isotopes). A labelled molecule, such as a labeled target molecule, may be distinguished from its unlabeled form by a difference in mass, e.g., by mass spectrometry. Stable isotope labelled molecules can be generated for any target molecule, such as a nucleic acid molecule, protein, drug, hormone, cell, pathogen, small molecule, or environmental toxin, so long as two differently stable isotope labeled versions of the same molecule each have a mass distinguishable from each other and from the native target molecule. Stable isotope labeled molecules can be used as stable isotope labeled standard (SIS) molecules, for purposes of assay calibration. Example stable isotopes used for labelling are $^{2}H$, $^{13}C$, $^{15}N$, $^{18}O$, and $^{34}S$. The terms "stable isotope labeled molecule" and "SIS molecule" are used interchangeably herein.

An unlabeled form of a standard isotope labelled molecule may have the same chemical structure as its stable isotope labeled counterpart but be comprised of unmodified elements with standard isotope numbers. For example, an unlabeled molecule can include standard elements (e.g., $^{1}H$, $^{12}C$, $^{14}N$, $^{16}O$, or $^{32}S$) whereas the stable isotope labeled molecule can include one or more isotopes (e.g., $^2$H, $^{13}$C, $^{15}$N, $^{18}$O, and $^{34}$S). Thus, a molecule in its unlabeled (e.g., native) form will have a distinguishable mass from its standard isotope labeled version.

Subject: Includes both human and veterinary subjects, such as humans, non-human primates, pigs, sheep, cows, rodents, birds, and the like, which can be the source of a test sample analyzed by the disclosed methods. An "animal" is a living, multi-cellular vertebrate organisms, a category that includes, for example, mammals and birds (e.g., chickens). The term mammal includes both human and non-human mammals. In two non-limiting examples, a subject is a human subject or a murine subject.

Target Molecules: Any substance whose detection, such as quantification, is desired. Examples of such molecules include nucleic acid molecules, proteins, peptides, a chemical compound, pathogen, drug, or toxin. Additional examples are provided herein.

Test Matrix: The sample milieu. In an example, the test matrix is a heterogeneous mixture in which a target molecule is to be assayed. In an example, the test matrix is a biological or environmental sample, such as blood, plasma, urine, tissue, groundwater, or a food sample. Thus, the test matrix can include native proteins, nucleic acids, small molecules, toxins, drugs, pathogens, or combinations thereof. In an example, a test matrix may also be a pooled standard (e.g., a pool of blood plasma from a commercial source) for assay purposes.

Test Sample: A sample comprising one or more target molecules for evaluation, such as quantification. The sample can be biological (e.g., from a subject) or environmental (e.g., from a water, air, or soil source, or a food source, or a plant source). In specific examples, test sample is a bodily fluid (e.g., blood plasma, urine, semen, or saliva), hair, feces, nails, skin, tissue (such as a tumor biopsy), organ, or dried blood spot. Additional examples are provided herein.

Quality Control (QC) Sample(s): A sample for assessment of testing and calibration accuracy. The quality control samples are distinct from the test sample(s) and the control sample(s) used in generating the calibration curve (e.g., the calibration control samples). Generally, fewer concentrations are needed for quality control than for a calibration curve, for example, a low, mid and high concentration samples may be utilized.

Methods for Quantifying Molecules

Precise and accurate quantitation of target molecules present in a sample containing a mixture of molecules (e.g., a complex sample) has several applications, including those in biological samples for diagnosing disease states and monitoring health. Precise quantitation requires calibration. Prior calibration methods have utilized an alternate test matrix for calibration assays. Utilizing a different test matrix for the calibration assays, these prior methods aimed to reduce interference from endogenous target molecules. In this way, an assay to detect target peptides in human blood plasma, for example, may have utilized chicken plasma as a test matrix in the creation of a calibration curve to avoid interference from endogenous peptides. The methods disclosed herein allow, but do not require, the same test matrix for sample preparation and standard preparation. The methods utilize two SIS labelled molecule versions of the target molecule, which are distinguishable from an endogenous target molecule, and thus not subject to interference from target molecules present in the test matrix of the control sample. Furthermore, the methods of the present application allow for external quality control samples in a same matrix assay which provide further data on testing accuracy.

Disclosed herein is a new approach to quantifying target molecules by mass spectrometry. The method uses two differentially labeled stable isotope standard (SIS) peptides, which allows external calibration curve and quality control (QC) samples to be prepared in a test matrix without interference from endogenous target molecules. In this way, both control samples and test samples can be prepared in the same test matrix, in contrast to prior methods which utilized a surrogate test matrix to limit noise from endogenous target molecules. The ability to prepare samples of known concentrations in the test matrix with one SIS molecule while using the second SIS molecule as the internal standard to uniformly normalize the analyte and standard signals in all sample types (standards, unknowns, and QC samples) improves the analytical performance of these assays.

The results provided herein shows the double-SIS-peptide calibration methods is an improvement on calibration methods that are currently used. The new method was evaluated on a multiplexed panel of 31 peptides of various sequence lengths, present at various endogenous concentrations, and with varying hydrophobicities. This method can replace reverse curves since it does not introduce accuracy bias in the measurement due to ratio flipping, while at the same time it can simplify method development and validation. In addition, the ability to directly measure accuracy can also help in harmonizing results between studies within the same laboratory or between laboratories. The disclosed calibration methods utilize two stable isotope labeled molecules, one as the calibrator and the other as the internal standard added uniformly to all samples. This method allows standard and quality control samples to be prepared in a test matrix (e.g., control human plasma) without complications due to interference from endogenous test molecules (e.g., proteins). With this method, assays more closely reflect the standards set by regulated bioanalysis. For example, assay accuracy can be determined directly in human plasma, which is not the case when only one labeled peptide is available. Moreover, the slopes of calibration curves are generated in plasma which avoids the need for comparing slopes generated in a different matrix with those in plasma.

Provided herein are methods of quantifying one or more target molecules in a test sample. The methods can be multiplexed, such as two or more target molecules are detected in a sample, or two or more different samples are analyzed for the same target molecule(s) for example simultaneously or contemporaneously. In some examples, at least 2, at least 3, at least 4, at least 5, at least 6, at least 7, at least 8, at least 9, at least 10, at least 20, or at least 30 different target molecules are quantified. If more than one target is detected in a sample, the targets are distinguishable by their mass, for example by mass spectrometry.

The methods can include adding a first stable isotope labeled molecule to a control sample at two or more different concentrations (such as at least 2, at least 3, at least 4, at least 5, at least 6, at least 7, at least 8, at least 9, or at least 10 different concentrations, such as 2, 3, 4, 5, 6, 7, 8, 9 or 10 different concentrations) and adding a second stable isotope labeled molecule to the control sample and to the test sample in a constant concentration. That is, the amount of second stable isotope labeled molecule added to the control sample and to the test sample is the same. The label of the first and second stable isotope labeled molecules are different such that the first stable isotope labeled molecule and the second stable isotope labeled molecule have distinguishable masses. In addition, the first and second stable isotope labeled molecules have masses that are distinguishable from the native target molecule in the test sample. The first SIS molecule used at varied concentrations may be referred to as a calibration standard. The second SIS molecule may be referred to as an internal standard.

Thus, for each target molecule to be detected and quantified, two different stable isotope labeled molecules are used, that allow for the target molecule, first stable isotope labeled molecule and second stable isotope labeled molecule to be distinguished from one other using mass spectrometry. For example, one stable isotope labeled molecule could include a single label (e.g., have one stable isotope on a single amino acid), while the second stable isotope labeled molecule could include a different single label, include two or more stable isotopes (such as two different stable isotopes, e.g., two different stable isotopes on a single amino acid, or the same stable isotope at two different locations on the molecule, e.g., on two different amino acids). The stable isotope labeled molecules are the same as the target, but for the presence of the stable isotope label(s). For example, if the target molecule is fibronectin, the first stable isotope labeled molecule can be a fibronectin containing a stable isotope and the second stable isotope labeled molecule can be a fibronectin containing a stable isotope distinguishable from the stable isotope on the first stable isotope labeled fibronectin. For example, the fibronectin containing the first stable isotope could have a stable isotope on a single amino acid, while the fibronectin containing the second stable isotope could have a stable isotope on two amino acids or have a single amino acid with two stable isotopes. If a peptide is the target (e.g., used as a surrogate for detecting the presence of a protein), the same principles apply. For example, if the target molecule is fibronectin, and the peptide used to determine the presence of fibronectin is SSPVVIDASTAIDAPSNLR (SEQ ID NO: 32), the first stable isotope labeled molecule can be a SSPVVIDASTAIDAPSNLR containing a stable isotope and the second stable isotope labeled molecule can be a SSPVVIDASTAIDAPSNLR containing a stable isotope distinguishable from the stable isotope on the first stable isotope labeled fibronectin. For example, the SSPVVIDASTAIDAPSNLR containing the first stable isotope could have a stable isotope on a single amino acid, while the SSPVVIDASTAIDAPSNLR containing the second stable isotope could have a stable isotope on two amino acids or have a single amino acid with two stable isotopes. Variations of this labeling are possible, as long as the first and second stable isotope labeled molecules are distinguishable from one another and from the native molecules via mass spectrometry (for example two stable isotopes on two different amino acids (one each)).

In the example provided above, a target molecule is a peptide used as a surrogate for detection (e.g., quantification) of a selected protein. Example peptides may be produced by enzymatic digestion (e.g., LysN, LysC, Glu-C, Asp-N, ArgC, pepsin, proteinase K, elastase, thermolysin, papain or subtilisin, or any combination thereof). Enzymatic digestion of a target can produce a number of peptides. A single assay may use any number of target peptides as surrogates for the same protein. For example, trypsin digestion of Serotransferrin produces both DGAGDVAFVK (SEQ ID NO: 7) and EGYYGYTGAFR (SEQ ID NO: 8), both of which may be used in a single assay.

Variations to stable isotope labeling include labeling of internal amino acids, the n-terminal amino acid, the c-terminal amino acid, or combinations thereof. One skilled in the art will appreciate that this strategy can be used for any target molecule of interest.

Figure 6:
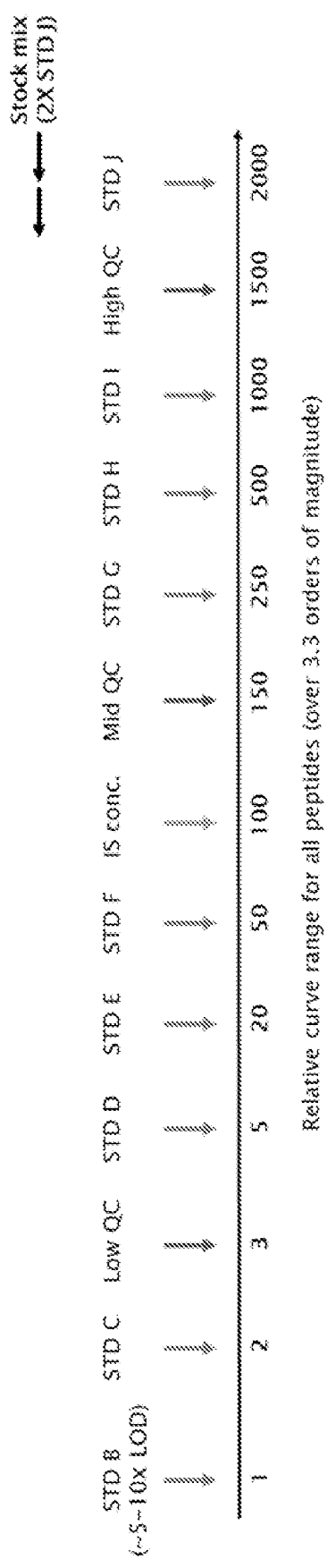
FIG. 6 is a schematic drawing of a calibration curve design and relative peptide concentrations for all peptides in each sample type.

A control sample can be used to generate a calibration curve, and thus be one of many samples of varying concentrations. A control sample can also be a quality control sample, e.g., a sample of one or more concentrations for ensuring calibration accuracy that is distinct from calibration control samples and the test sample. Quality control samples are prepared similarly to the calibration control samples but provide an independent assessment of assay accuracy. Quality control samples can contain fewer overall concentrations of a calibration standard corresponding to, for example, mid, low and high concentrations spanning the calibration standard concentrations used for creation of the calibration curve. An example selection of quality control sample calibration standard concentrations is illustrated in FIG. 6, where a low, mid and high concentration quality control sample are used at three different points among a calibration curve span. In the example shown in FIG. 6, the quality control sample calibration standard concentrations are distinct from the calibration standard concentrations used in calibration control samples, this is shown graphically in FIG. 3B.

A detection instrument, such as a mass spectrometer, is used to detect or measure the presence of the SIS molecules in the control and test samples, and the target molecule in the test sample. An instrument signal magnitude from the detection instrument is measured for the target molecule, the first SIS molecule (calibration standard) and a second SIS molecule (internal standard). In some examples no target molecule will be detected, e.g., when no target molecule is present in the test sample, or when a test matrix is used in the control samples that does not contain the target molecule. Exemplary instrument signal magnitudes include intensity, counts, area under a curve, or combinations thereof.

A calibration curve is calculated or generated from the control sample, using the ratios of the first SIS molecule (calibration standard) to the second SIS molecule (internal standard) and plotting the ratios against the known concentrations of the first SIS molecule (calibration standards). The calibration standards can be used in a number of different concentrations, e.g., 2, 3, 4, 5, 6, 7, 8, 9, 10, 11, 12, 13, 14, 15 or more different concentrations. The calibration standard concentrations can be serial dilutions, for example the concentrations may differ by a factor of 2, 3, 4, 5, 6, 7, 8, 9, 10, or more. The calibration standard concentrations should span a suspected concentration of target molecule (see for example, FIG. 6). The internal standards are used in a uniform concentration among each of the calibration standards containing control samples, the test sample, and any quality control sample. The generated calibration plot is fit with a best fit line. The best fit may be linear or curved.

Quantification of the one or more target molecules is achieved by plotting or generating the ratio of the instrument signal magnitude of the target molecule in the test sample to the test instrument signal magnitude of the second SIS molecule (internal standard) in the test sample, and aligning the resultant ratio with the best fit line and extrapolating the concentration of the target molecule in the sample.

In a specific embodiment, the methods disclosed herein are used to quantify target peptides in a test sample, such as human blood plasma. Control samples can be created by addition of a dilution curve (e.g., two or more or three or more different concentrations, or a serial dilution) of a stable isotope labeled peptide (calibration standard) in the test matrix. The test matrix can be blood plasma, such as commercially available pooled blood plasma (e.g., from Innovative Research, Cat. No.: Catalog No.: IPLA-N). If no suitable pooled standard is available, the test sample, or its equivalent (e.g., comparable matrix from a different subject, species, etc.) can be used as a matrix for the control samples. To each of the control samples of the dilution curve, the second stable isotope labeled peptide (internal standard) of a distinguishable weight is added in a uniform concentration. It should be understood that many different versions of the first and second SIS compounds may be utilized simultaneously (e.g., peptides from multiple proteins and/or multiple peptides of the same protein can each be used in their two different labeled forms). The second stable labelled peptide isotope (internal standard) is also added to the test sample in a uniform concentration (e.g., the same concentration used for the control samples). Mass spectrometry can be used to assess the mass of the two stable isotope labelled peptides in the control sample and of the single, constant concentration SIS peptide and target peptide in the test sample. The ratio of the peak area (area under the curve) of the first SIS peptide to the second SIS peptide is calculated and plotted against concentration to produce a calibration curve with a best fit line. The target peptide is quantified by mapping the ratio of the target peptide to the single, constant concentration, SIS peptide onto the calibration curve and solving for the unknown concentration.

The disclosed methods also allow for use of independent quality control samples to ensure test accuracy. In the same way a control sample is prepared with varied concentrations of one SIS molecule and a consistent concentration of the other SIS molecule, quality control samples can be prepared with one or more concentrations of a first SIS molecule. In some embodiments, quality control samples are prepared for a low and high concentration of SIS molecule. In some embodiments, quality control samples are prepare for a low, mid and high, or more intervening concentrations of a first SIS molecule.

The methods of quantifying target molecules disclosed herein allow for calibration and quality control assays to be performed in a test matrix identical to that of the test sample. Performing calibration and quality control assays in a matrix identical to that of the test sample allows for greater accuracy of quantification. These more precise methods also align with FDA guidelines for monitoring biological samples[8]. These methods allow for calibration assays to be performed in a test matrix free from interference from endogenous target molecules.

Test Samples

The test sample analyzed can be any biological or environmental specimen that may contain (or is known to contain or is suspected of containing) one or more target molecules. Biological samples are usually obtained from a subject and can include genomic DNA, cDNA, RNA (including mRNA and miRNA), protein, peptides, or combinations thereof. Examples include a tissue or tumor biopsy, fine needle aspirate, bronchoalveolar lavage, pleural fluid, spinal fluid, saliva, sputum, surgical specimen, lymph node fluid, ascites fluid, peripheral blood (such as serum or plasma), dried blood spots, urine, feces, buccal swab, and autopsy material. Techniques for acquisition of such samples are known (for example see Schluger et al. *J. Exp. Med.* 176:1327-33, 1992, for the collection of serum samples). Serum or other blood fractions can be prepared in the conventional manner. Samples can also include fermentation fluid and tissue culture fluid.

Environmental samples include those obtained from an environmental media, such as water, air, soil, dust, wood, plants or food.

In one example the test sample is a food sample, such as a meat, fruit, dairy, or vegetable sample. For example, using the methods provided herein, adulterants in food products can be detected, such as a pathogen or toxin or other harmful product.

Once a sample has been obtained, the sample can be used directly, concentrated (for example by centrifugation or filtration), purified, liquefied, lysed, diluted in a fluid, or combinations thereof. In some examples, cells, proteins or nucleic acids or pathogens are extracted from the sample, and the resulting preparation (such as one that includes isolated proteins) analyzed using the methods provided herein.

Control Samples

Control samples can be used in calibration of assay conditions, confirmation of testing accuracy, or both. Control samples can include samples for the creation of a calibration curve (e.g., calibration control samples) and those for quality control (e.g., quality control samples). Calibration control samples include individual samples, each containing a different concentration of a stable isotope labeled calibration standard. Furthermore, each calibration control sample contains a uniform concentration of an internal standard. Concentrations of calibration standard used in the control sample are selected to span a suspected control of the target molecule.

Control samples can further include an independent set or single sample used in assaying testing accuracy, e.g., quality control samples. Quality control samples are prepared similarly to the calibration control samples, but provide an independent assessment of assay accuracy. Quality control samples can contain fewer overall concentrations of a calibration standard corresponding to, for example, mid, low and high concentrations spanning the calibration standard concentrations used for creating the calibration curve. An example selection of quality control sample calibration standard concentrations is illustrated in FIG. 6, where a low, mid and high concentration quality control sample are used at three different points among a calibration curve span. In the example of FIG. 6, the quality control sample calibration standard concentrations are distinct from the calibration standard concentrations used in calibration control samples; this is shown graphically in FIG. 3B.

Using the two SIS methods disclosed herein, control samples can be formulated in the test matrix. For example, the calibration standard and the internal standard can be added to an assay milieu that is identical to that of the test sample. The test matrix can be a biological or environmental sample, such as blood, plasma, urine, tissue, groundwater, or a food sample (or any other sample described herein). Thus, the test matrix can include native proteins, nucleic acids, small molecules, toxins, drugs, pathogens, or combinations thereof. In an example, a test matrix may also be a pooled standard (e.g., a pool of blood plasma from a commercial source) for assay purposes.

Traditional calibration methods may have used a test matrix that differed from a sample matrix, for example chicken and not human blood plasma when analyzing a human blood plasma test sample, in an effort to reduce noise from endogenous target molecules. The present methods allow for calibration within the test matrix. The test matrix in which a target molecule may be quantified may be any matrix suspected to contain a given target molecule. In some embodiments, a test matrix is a bodily sample, for example is whole blood, plasma, serum, urine, saliva, cerebral spinal fluid, tears, tumors, tissue biopsy, organ, hair, etc. In some embodiments, a test matrix is an environmental sample, e.g., ground or surface water (such as fresh water, brackish water, or salt water), crude oil, soil, etc. In some embodiments, a test matrix is any sample suitable to undergo analysis by mass spectrometry.

Exemplary Target Molecules

The disclosed methods can be designed to detect any target of interest for which two stable isotope labeled standards can be created which are distinguishable by mass. Exemplary target agents are provided herein; however one skilled in the art will appreciate that other target agents can be detected with the disclosed methods.

A target molecule can be any molecule detectable by mass spectrometry, such as one with a mass-to-charge ratio range of about 1-5000 m/z, about 1-4000 m/z, about 1-3000 m/z, about 1-2000 m/z, about 1-1000 m/z, etc. In addition, a target molecule is modifiable with stable isotope labelling to create two distinct SIS standard molecules with distinguishable masses. An SIS standard for a particular target molecule can be any molecule that can be modified to incorporate one or more stable isotopes, e.g., $^2$H, $^{13}$C, $^{15}$N, $^{34}$S that give the labeled molecule distinguishable mass from the unlabeled form and also from a second stable isotope labeled version.

The disclosed methods are suitable, but not exclusively, for multiplexed assays, particularly in complex samples comprising many target molecules to be quantified. In embodiments, the methods are used to quantify at least 2, at least 3, at least 4, at least 5, at least 10, at least 20, at least 50, or at least 100 different target molecules, such as about 1, 2, 3, 4, 5, 6, 7, 8, 9, 10, 15, 20, 25, 30, 35, 40, 45, 50, 55, 60, 65, 70, 75, 80, 85, 90, 95, 100 or more target molecules, or any intervening integer thereof. The present methods can allow for greater accuracy in quantifying target molecules. For example, the percent error of the method is less than about 100%, 90%, 80%, 70%, 60%, 50%, 45%, 40%, 35%, or 30%.

The target molecule may be a biomarker, such as for example, nucleic acid molecule, protein, metabolite, hormone, small molecule, metal, etc. Thus, target molecules to be assayed using the present methods may be used in the diagnosis, prognosis, or treatment selection for disease states. Example disease states that can be evaluated by quantitation of biomarkers using the present methods are cancer, cardiovascular disease, kidney disease, liver disease, infection, etc. The disclosed methods can be used in assessing the health of a subject for purposes of restoring or maintaining health, such as by alleviating the symptoms associated with a disease or physiological disorder, or delaying (including preventing) progression or onset of a disease.

Target molecules to be detected in a subject may also be foreign substances, to be detected for example in a toxicity or drug panel. Monitoring of foreign substance target molecule quantities in a subject may be useful, for example in the evaluation of drug metabolism for purposes of treatment, dosing, etc.

In embodiments, target molecules may also be environmental toxins, for example, small molecules, metals, pathogens, nucleic acid molecules, or peptides indicative of industrial or agricultural runoff in a watershed.

In embodiments, target molecules are those associated with food contamination, such as pathogens, nucleic acid molecules, or peptides indicative of food spoilage.

Metals

In one example the target agent is a metal (e.g., elements, compounds, or alloys that have high electrical conductivity), such as a heavy metal or a nutritional metal. Metals occupy the bulk of the periodic table, while non-metallic elements can only be found on the right-hand-side of the Periodic Table of the Elements. A diagonal line drawn from boron (B) to polonium (Po) separates the metals from the nonmetals. Most elements on this line are metalloids, sometimes called semiconductors. Elements to the lower left of this division line are called metals, while elements to the upper right of the division line are called non-metals.

Heavy metals include any metallic chemical element that has a relatively high density and is toxic, highly toxic or poisonous at low concentrations. Examples of heavy metals include mercury (Hg), cadmium (Cd), arsenic (As), chromium (Cr), thallium (Tl), uranium (U), plutonium (Pu), and lead (Pb).

Nutritional metal ions include those important in animal nutrition and may be necessary for particular biological functions, include calcium, iron, cobalt, magnesium, manganese, molybdenum, zinc, cadmium, and copper.

Pathogens/Microbes

Any pathogen or microbe can be detected using the methods provided herein, for example in a patient sample, food sample, or environmental sample. Detection of pathogens/microbes can be by detection of a unique marker on, in, or released by a target microbe or pathogen. In some examples, detection of such agents is used to diagnose an infection in a subject.

For example, particular antimicrobial antigens and nucleic acid molecules (such as DNA or RNA), as well as bacterial spores, can be detected. In some examples, a particular microbial cell is detected, or a particular virus. In some examples, intact microbes are detected, for example by detecting a target surface protein (such as a receptor). In other examples, a conserved DNA or RNA specific to a target microbe is detected. In some examples, an antibody specific for the target microbe is detected.

Exemplary pathogens include, but are not limited to, viruses, bacteria, fungi, nematodes, and protozoa. A non-limiting list of pathogens that can be detected using the methods provided herein are provided below.

For example, viruses that can be detected with the disclosed methods include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepatoviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); Calciviridae (which includes Norovirus and Sapovirus); and Coronaviruses (examples of which include SARS coronaviruses, such as the Urbani strain). Exemplary negative-strand RNA viruses include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses).

Viruses that can be detected with the disclosed methods include DNA viruses. DNA viruses include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

Another group of viruses that can be detected with the disclosed methods includes Retroviruses. Examples of retroviruses include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

In one example, the virus detected with the disclosed methods is one or more of the following: HIV (for example an HIV antibody, p24 antigen, or HIV genome); Hepatitis A virus (for example an Hepatitis A antibody, or Hepatitis A viral genome); Hepatitis B (HB) virus (for example an HB core antibody, HB surface antibody, HB surface antigen, or HB viral genome); Hepatitis C (HC) virus (for example an HC antibody, or HC viral genome); Hepatitis D (HD) virus (for example an HD antibody, or HD viral genome); Hepatitis E virus (for example a Hepatitis E antibody, or HE viral genome); a respiratory virus (such as influenza A & B, respiratory syncytial virus, human parainfluenza virus, or human metapneumovirus), or West Nile Virus.

In one example, the method can distinguish between an infectious versus a non-infectious virus.

Pathogens that can be detected with the disclosed methods also include bacteria. Bacteria can be classified as gram-negative or gram-positive. Exemplary gram-negative bacteria include, but are not limited to: *Escherichia coli* (e.g., K-12 and O157:H7), *Shigella dysenteriae*, and *Vibrio cholerae*. Exemplary gram-positive bacteria include, but are not limited to: *Bacillus anthracis, Staphylococcus aureus, Listeria*, pneumococcus, gonococcus, and streptococcal meningitis. In one example, the bacteria detected with the disclosed methods and sensors is one or more of the following: Group A *Streptococcus*; Group B *Streptococcus*; *Helicobacter pylori*; Methicillin-resistant *Staphylococcus aureus*; Vancomycin-resistant enterococci; *Clostridium difficile; E. coli* (e.g., Shiga toxin producing strains); *Listeria; Salmonella; Campylobacter; B. anthracis* (such as spores); *Chlamydia trachomatis*; and *Neisseria gonorrhoeae*.

Protozoa, nemotodes, and fungi are also types of pathogens that can be detected with the disclosed methods. Exemplary protozoa include, but are not limited to, *Plasmodium* (e.g., *Plasmodium falciparum* to diagnose malaria), *Leishmania, Acanthamoeba, Giardia, Entamoeba, Cryptosporidium, Isospora, Balantidium, Trichomonas, Trypanosoma* (e.g., *Trypanosoma brucei*), *Naegleria*, and *Toxoplasma*. Exemplary fungi include, but are not limited to, *Coccidiodes immitis* and *Blastomyces dermatitidis*.

In one example, bacterial spores are detected. For example, the genus of *Bacillus* and *Clostridium* bacteria produce spores that can be detected. Thus, *C. botulinum, C. perfringens, B. cereus*, and *B. anthracis* spores can be detected (for example detecting anthrax spores). One will also recognize that spores from green plants can also be detected using the methods provided herein.

Nucleic Acids

The disclosed methods also permit detection of nucleic acid molecules, such DNA and RNA, such as a DNA or RNA sequence that is specific for a particular nucleic acid molecule, pathogen or cell of interest. For example, target pathogens can have conserved DNA or RNA sequences specific to that pathogen (for example conserved sequences are known in the art for HIV, bird flu and swine flu), and target cells may have specific DNA or RNA sequences unique to that cell, or provide a way to distinguish a target cell from another cell (such as distinguish a tumor cell from a benign cell).

In some examples, a target sequence is selected that is associated with a disease or condition, such that detection of the target nucleic acid can be used to infer information (such as diagnostic or prognostic information for the subject from whom the sample is obtained) relating to the disease or condition.

In specific non-limiting examples, a target nucleic acid sequence associated with a tumor (for example, a cancer) is detected. Numerous chromosome abnormalities (including translocations and other rearrangements, reduplication (amplification) or deletion) have been identified in neoplastic cells, especially in cancer cells, such as B cell and T cell leukemias, lymphomas, breast cancer, colon cancer, neurological cancers and the like.

Exemplary target nucleic acids include, but are not limited to: the SYT gene located in the breakpoint region of chromosome 18q11.2 (common among synovial sarcoma soft tissue tumors); HER2, also known as c-erbB2 or HER2/neu (a representative human HER2 genomic sequence is provided at GENBANK™ Accession No. NC_000017, nucleotides 35097919-35138441) (HER2 is amplified in human breast, ovarian, gastric, and other cancers); p16 (including D9S1749, D9S1747, p16(INK4A), p14(ARF), D9S1748, p15(INK4B), and D9S1752) (deleted in certain bladder cancers); EGFR (7p12; e.g., GENBANK™ Accession No. NC_000007, nucleotides 55054219-55242525), MET (7q31; e.g., GENBANK™ Accession No. NC_000007, nucleotides 116099695-116225676), C-MYC (8q24.21; e.g., GENBANK™ Accession No. NC_000008, nucleotides 128817498-128822856), IGF1R (15q26.3; e.g., GENBANK™ Accession No. NC_000015, nucleotides 97010284-97325282), D5S271 (5p15.2), KRAS (12p12.1; e.g., GENBANK™ Accession No. NC_000012, complement, nucleotides 25249447-25295121), TYMS (18p11.32; e.g., GENBANK™ Accession No. NC_000018, nucleotides 647651-663492), CDK4 (12q14; e.g., GENBANK™ Accession No. NC_000012, nucleotides 58142003-58146164, complement), CCND1 (11q13, GENBANK™ Accession No. NC_000011, nucleotides 69455873-69469242), MYB (6q22-q23, GENBANK™ Accession No. NC_000006, nucleotides 135502453-135540311), lipoprotein lipase (LPL) (8p22; e.g., GENBANK™ Accession No. NC_000008, nucleotides 19840862-19869050), RB1 (13q14; e.g., GENBANK™ Accession No. NC_000013, nucleotides 47775884-47954027), p53 (17p13.1; e.g., GENBANK™ Accession No. NC_000017, complement, nucleotides 7512445-7531642), N-MYC (2p24; e.g., GENBANK™ Accession No. NC_000002, complement, nucleotides 15998134-16004580), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), aALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054-69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994017-28026515); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89718512), AKT2 (19q13.1-q13.2; e.g., GENBANK™ Accession No. NC_000019, complement, nucleotides 45428064-45483105), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In examples where the target molecule is a nucleic acid molecule, the sample to be tested can be treated with agents that permit disruption of the cells or pathogen.

Recreational and Other Drugs

The disclosed methods also permit detection of a variety of drugs, such as pharmaceutical or recreational drugs, such as tetrahydrocannabinol, heroin, cocaine, caffeine, and methamphetamine.

For example, the presence of caffeine, cocaine, opiates and opioids (such as oxycodone), *cannabis* (for example by detecting tetrahydrocannabinol (THC)), heroin, methamphetamines, crack, ethanol, acetaminophen, benzodiazepines, methadone, phencyclidine, or tobacco (for example by detecting nicotine), can be detected using the disclosed methods. In one example, the target is a therapeutic drug, such as a chemotherapeutic, antibiotic, such as theophylline, methotrexate, tobramycin, cyclosporine, rapamycin, or chloramphenicol.

Cells

The disclosed methods also permit detection of a variety of cells, such as tumor or cancer cells, as well as other diseased cells. Detection of cells can be by detection of a unique marker on (such as a tumor associated antigen), in, or released by a target cell. In one example, the methods can distinguish between a tumor cell and a normal cell of the same cell type, such as a normal breast cell from a cancerous breast cell. Tumors are abnormal growths which can be either malignant or benign, solid or liquid (for example, hematogenous). In some examples, cells are detected by detecting a protein or nucleic acid molecule specific for that cell type.

Examples of hematological tumors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate-, and high-grade), multiple myeloma, Waldenström's macroglobulinemia, heavy chain disease, myelodysplastic syndrome, mantle cell lymphoma and myelodysplasia.

Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Thus, in some examples the sensors and devices provided herein permit detection of such tumor cells using the disclosed methods.

Proteins/Peptides

The disclosed method permit detection of proteins, such as cell surface receptors, cytokines, antibodies, hormones, as well as toxins. In some examples, a target protein is associated with a disease or condition, such that detection (or absence) of the target protein can be used to infer information (such as diagnostic or prognostic information for the subject from whom the sample is obtained) relating to the disease or condition.

In embodiments, the target molecule is a peptide. A target peptide can be any fragment, portion or whole of a protein of interest. Thus, a peptide can be detected as a surrogate for a full-length protein in the sample. In some examples, a target peptide is an enzyme-digested fragment of a selected protein, such as digestion by trypsin, chymotrypsin, LysN, LysC, Glu-C, Asp-N, ArgC, pepsin, proteinase K, elastase, thermolysin, papain, subtilisin, or combinations thereof.

In one example the protein detected is a cytokine. Cytokines are small proteins secreted by immune cells that have effects on other cells. Examples include interleukins (IL) and interferons (IFN), and chemokines, such as IL-1, IL-2, IL-4, IL-6, IL-8, IL-10, IFN-γ, IFN-β, transforming growth factor (TGF-β), and tumor necrosis factor (TNF)-α.

In one example the protein detected is a hormone. A hormone is a chemical messenger that transports a signal from one cell to another. Examples include plant and animal hormones, such as endocrine hormones or exocrine hormones. Particular examples include follicle stimulating hormone (FSH), human chorionic gonadotropin (hCG), thyroid stimulating hormone (TSH), growth hormone, progesterone, and the like.

In yet another example the protein detected is a toxin. Toxins are poisonous substances produced by cells or organisms, such as plants, animals, microorganisms (including, but not limited to, bacteria, viruses, fungi, rickettsiae or protozoa). Particular examples include botulinum toxin, ricin, diphtheria toxin, Shiga toxin, Cholera toxin, Staphylococcal enterotoxin B, and anthrax toxin. In another example, the toxin is an environmental toxin. In one example the toxin is a mycotoxin, such as: aflatoxin, citrinin, ergot alkaloids, patulin, *fusarium* toxins, or ochratoxin A. In one example the toxin is a cyanotoxin, such as: microcystins, nodularins, anatoxin-a, aplysiatoxins, cylindrospermopsins, lyngbyatoxin-a, and saxitoxins. In one example the toxin is an endotoxin, hemotoxin, necrotoxin, neurotoxin, or cytotoxin.

In one example, the target protein detected is a tumor-associated or tumor-specific antigen, such as CA-125 (ovarian cancer), alphafetoprotein (AFP, liver cancer marker); carcinoembryonic antigen (CEA; bowel cancers); HER1, HER2, and MUC-1 (breast cancer); CD20 (non-Hodgkin lymphoma); CD25 (T-cell lymphoma); CD33 (acute myelogenous leukemia; CD52 (chronic lymphocytic leukemia); Lewis Y (colorectal cancer, biliary cancer); TAG72 (adenocarcinomas including colorectal, pancreatic, gastric, ovarian, endometrial, mammary, and non-small cell lung cancer); MAGE (malignant melanoma); and vascular endothelial growth factor (colorectal cancer).

In one example the target protein is a fertility-related biomarker, such as hCG, luteinizing hormone (LH), follicle-stimulating hormone (FSH), or fetal fibrinogen.

In one example the target protein is a diagnostic protein, such as prostate-specific antigen (PSA, for example GenBank Accession No. NP_001025218), C reactive protein, cyclic citrullinate peptides (CCP, for example to diagnose rheumatoid arthritis) or glycated hemoglobin (Hb A1c). In another example, the protein is one found on the surface of a target microbe or cell, such as a bacterial cell, virus, spore, or tumor cell. Such proteins, such as receptors, may be specific for the microbe or cell (for example HER2, IGF1R, EGFR or other tumor-specific receptor noted below in "nucleic acids"). In one example the protein is prostate-specific antigen (PSA, for example GenBank Accession No. NP_001025218).

Example peptide biomarkers that can be assayed using the disclosed methods include ACTH or corticotropin, Afamin, Alanine aminotransferase, Alkaline Phosphatase, Alpha-1-acid glycoprotein 1, Alpha-1-antichymotrypsin (Alpha-1-Antitrypsin), Alpha-1-antitrypsin, Alpha-1B-glycoprotein, Alpha-2-HS-glycoprotein, Alpha-2-macroglobulin, Angiogenin, Angiotensin Conv. Enz., Angiotensinogen, Antinuclear antibody, Antithrombin-III, Apolipoprotein A, Apolipoprotein A-I, Apolipoprotein A-II, Apolipoprotein A-IV, Apolipoprotein B-100, Apolipoprotein C-I, Apolipoprotein C-II, Apolipoprotein C-III, Apolipoprotein C-IV, Apolipoprotein D, Apolipoprotein E, Apolipoprotein F, Apolipoprotein L1, Apolipoprotein M, Aspartate aminotransferase, Beta-2-microglobulin, Beta-Ala-His dipeptidase, Biotinidase, C4b-binding protein alpha chain, CA 125, CA 15-3, CA 19-9, Cadherin-5, Calcitonin, Carbonic anhydrase 1, Cathelicidin antimicrobial peptide, CD44 antigen, CEA, Ceruloplasmin, Cholinesterase, Citrulline antibody, Clusterin, Coagulation factor X, Coagulation factor XI, Coagulation factor XII, Coagulation factor XIII A chain, Complement C1q subcomponent subunit A, Complement C1q subcomponent subunit B, Complement C1q subcomponent subunit C, Complement C1r subcomponent, Complement C1s subcomponent, Complement C2, Complement C3, Complement C4-B, Complement C5, Complement component C6, Complement component C9, Complement factor B, Complement factor H, Complement factor I, Corticosteroid-binding globulin, C-reactive protein, Creatine kinase (M-type), Cryoglobulin, Cystatin-C, Endothelial protein C receptor, Erythropoietin, Extracellular matrix protein 1, Factor V, Ferritin (light and heavy chains), Fetuin-B, Fibrinogen alpha chain, Fibrinogen beta chain, Fibrinogen gamma chain, Fibrinopeptide A, Fibronectin, Fibulin-1, Ficolin-2, Ficolin-3, Fructose-bisphosphate aldolase B, FSH, G6PD, Galectin-3-binding protein, Gamma-Glu transferase, Gastrin, Gelsolin, Glutathione peroxidase 3, Glycated hemoglobin, Growth hormone, Haptoglobin, hCG, Hemoglobin subunit alpha 1, Hemopexin, Heparin cofactor 2, Histidine-rich glycoprotein, HLA-B27, Ig kappa chain V-IV region, Ig mu heavy chain disease protein, IGF-1, Insulin, Insulin-like growth factor binding protein acid labile subunit, Insulin-like growth factor-binding protein 2, Insulin-like growth factor-binding protein 3, Insulin-like growth factor-binding protein complex acid labile subunit, Inter-alpha-trypsin inhibitor heavy chain H2, Inter-alpha-trypsin inhibitor heavy chain H4, Intercellular adhesion molecule 1, Kininogen-1, LDH, Leucine-rich alpha-2-glycoprotein 1, Lipase, Lipopolysaccharide-binding protein, L-selectin, Lumican, Mannan-binding lectin serine protease 2, Mannose-binding protein C, MRNA for apolipoprotein E, Mucin-16, Myoglobin, Phospholipid transfer protein, Pigment epithelium-derived factor, Plasma serine protease inhibitor, Plasminogen, Pregnancy zone protein, Prolactin, Protein S100-A9, Protein Z-dependent protease inhibitor, PSA, Retinol-binding protein 4, Serotransferrin, Serum albumin, Serum Amylase, Serum amyloid A-1 protein, Serum amyloid A-4 protein, Serum amyloid P-component, Serum paraoxonase/lactonase 3, Sex hormone-binding globulin, Tenascin, Tetranectin, Thyroglobulin, Thyroxine-binding globulin, Transthyretin, Troponin, Vasorin, Vitamin D-binding protein, Vitamin K-dependent protein C, Vitamin K-dependent protein S, Vitamin K-dependent protein Z, Vitamin K-dependent protein Z variant 1, Vitronectin, von Willebrand Factor, Xaa-Pro dipeptidase, and Zinc-alpha-2-glycoprotein.

Moreover, Table 1 below provides non-limiting examples of human blood plasma proteins that may be used as target molecules with corresponding first and second SIS molecules.

TABLE 1

Example human blood plasma proteins for detection

| Accession Number | UniProt Protein Name |
| --- | --- |
| P10809 | 60 kDa heat shock protein mitochondrial |
| P08253 | 72 KDa type IV collagenase |
| P11021 | 78 kDa glucose-regulated protein |
| O95450 | A disintegrin and metalloproteinase with thrombospondin motifs 2 |
| P59510 | A disintegrin and metalloproteinase with thrombospondin motifs 20 |
| Q9P2N4 | A disintegrin and metalloproteinase with thrombospondin motifs 9 |
| P62736 | Actin alpha cardiac muscle 1 |
| Q9HDC9 | Adipocyte plasma membrane-associated protein |
| Q15848 | Adiponectin |
| P35318 | ADM |
| P43652 | Afamin |
| P02763 | Alpha-1-acid glycoprotein 1 |
| P01011 | Alpha-1-antichymotrypsin |
| P01009 | Alpha-1-antitrypsin |
| P04217 | Alpha-1B-glycoprotein |
| P08697 | Alpha-2-antiplasmin |
| P02765 | Alpha-2-HS-glycoprotein |
| P01023 | Alpha-2-macroglobulin |
| P03950 | Angiogenin |
| Q9Y5C1 | Angiopoietin-related protein 3 |
| P01019 | Angiotensinogen |
| P01008 | Antithrombin-III |
| P02647 | Apolipoprotein A-I |
| P02652 | Apolipoprotein A-II |
| P06727 | Apolipoprotein A-IV |
| P04114 | Apolipoprotein B-100 |
| P02654 | Apolipoprotein C-I |
| P02655 | Apolipoprotein C-II |
| P02656 | Apolipoprotein C-III |

TABLE 1-continued

Example human blood plasma proteins for detection

| Accession Number | UniProt Protein Name |
|---|---|
| P55056 | Apolipoprotein C-IV |
| P05090 | Apolipoprotein D |
| P02649 | Apolipoprotein E |
| Q13790 | Apolipoprotein F |
| O14791 | Apolipoprotein L1 |
| O95445 | Apolipoprotein M |
| P08519 | Apolipoprotein(a) |
| P11511 | Aromatase |
| P16066 | Atrial natriuretic peptide receptor 1 |
| O75882 | Attractin |
| Q8WXX7 | Autism susceptibility gene 2 protein |
| Q8NDB2 | B-cell scaffold protein with ankyrin repeats |
| P02749 | Beta-2-glycoprotein 1 |
| P61769 | Beta-2-microglobulin |
| Q96KN2 | Beta-Ala-His dipeptidase |
| P01138 | Beta-nerve growth factor |
| P43251 | Biotinidase |
| P04003 | C4b-binding protein alpha chain |
| P55290 | Cadherin-13 |
| P33151 | Cadherin-5 |
| P01258 | Calcitonin |
| P06881 | Calcitonin gene-related peptide |
| P51911 | Calponin-1 |
| P00915 | Carbonic anhydrase 1 |
| Q96IY4 | Carboxypeptidase B2 |
| P15169 | Carboxypeptidase N catalytic chain |
| P22792 | Carboxypeptidase N subunit 2 |
| Q9NQ79 | Cartilage acidic protein 1 |
| P49913 | Cathelicidin antimicrobial peptide |
| P11717 | Cation-independent mannose-6-phosphate receptor |
| P29965 | CD40 ligand |
| P16070 | CD44 antigen |
| O43866 | CD5 antigen-like |
| B7Z2X4 | cDNA FLJ53327 highly similar to Gelsolin |
| P00450 | Ceruloplasmin |
| P11597 | Cholesteryl ester transfer protein |
| P06276 | Cholinesterase |
| P10645 | Chromogranin-A |
| P10909 | Clusterin |
| P00740 | Coagulation factor IX |
| P12259 | Coagulation factor V |
| P08709 | Coagulation factor VII |
| P00451 | Coagulation factor VIII |
| P00742 | Coagulation factor X |
| P03951 | Coagulation factor XI |
| P00748 | Coagulation factor XII |
| P00488 | Coagulation factor XIII A chain |
| P05160 | Coagulation factor XIII B chain |
| P02452 | Collagen alpha-1(I) chain |
| P02461 | Collagen alpha-1(III) chain |
| P39060 | Collagen alpha-1(XVIII) chain |
| P08123 | Collagen alpha-2(I) chain |
| P02746 | Complement C1q subcomponent subunit B |
| P02747 | Complement C1q subcomponent subunit C |
| P00736 | Complement C1r subcomponent |
| Q9NZP8 | Complement C1r subcomponent-like protein |
| P09871 | Complement C1s subcomponent |
| P06681 | Complement C2 |
| P01024 | Complement C3 |
| P0C0L4\|P0C0L5 | Complement C4-A |
| P0C0L4\|P0C0L5 | Complement C4-B |
| P01031 | Complement C5 |
| P13671 | Complement component C6 |
| P10643 | Complement component C7 |
| P07357 | Complement component C8 alpha chain |
| P07358 | Complement component C8 beta chain |
| P02748 | Complement component C9 |
| P00751 | Complement factor B |
| P00746 | Complement factor D |
| P08603 | Complement factor H |
| P05156 | Complement factor I |
| P08185 | Corticosteroid-binding globulin |
| P02741 | C-reactive protein |
| P12277 | Creatine kinase B-type |
| P06732 | Creatine kinase M-type |
| P01034 | Cystatin-C |
| P15924 | Desmoplakin |
| O94907\|Q9UBU2 | Dickkopf-related protein 1 |
| Q01459 | Di-N-acetylchitobiase |
| P15502 | Elastin |
| Q9Y5X9 | Endothelial lipase |
| Q9UNN8 | Endothelial protein C receptor |
| P00533 | Epidermal growth factor receptor |
| P16581 | E-selectin |
| Q16610 | Extracellular matrix protein 1 |
| P05413 | Fatty acid-binding protein heart |
| P02794 | Ferritin heavy chain |
| P02792 | Ferritin light chain |
| Q9UGM5 | Fetuin-B |
| P02671 | Fibrinogen alpha chain |
| P02675 | Fibrinogen beta chain |
| P02679 | Fibrinogen gamma chain |
| P02751 | Fibronectin |
| P23142 | Fibulin-1 |
| Q15485 | Ficolin-2 |
| O75636 | Ficolin-3 |
| Q12841 | Follistatin-related protein 1 |
| P05062 | Fructose-bisphosphate aldolase B |
| P17931 | Galectin-3 |
| Q08380 | Galectin-3-binding protein |
| P09104 | Gamma-enolase |
| P06396 | Gelsolin |
| P14136 | Glial fibrillary acidic protein |
| Q12879 | Glutamate receptor ionotropic NMDA 2A |
| Q13224 | Glutamate receptor ionotropic NMDA 2B |
| P22352 | Glutathione peroxidase 3 |
| P09211 | Glutathione S-transferase P |
| P00738 | Haptoglobin |
| P04792 | Heat shock protein beta-1 |
| P69905 | Hemoglobin subunit alpha |
| P02790 | Hemopexin |
| P05546 | Heparin cofactor 2 |
| P26927 | Hepatocyte growth factor-like protein |
| P04196 | Histidine-rich glycoprotein |
| Q86YZ3 | Hornerin |
| Q14520 | Hyaluronan-binding protein 2 |
| P01857 | Ig gamma-1 chain C region |
| P06312 | Ig kappa chain V-IV region |
| P01871 | Ig mu chain C region |
| P04220\|P01871 | Ig mu heavy chain disease protein |
| Q9Y6R7 | IgGFc-binding protein |
| P05019 | Insulin-like growth factor I |
| P08833 | Insulin-like growth factor-binding protein 1 |
| P18065 | Insulin-like growth factor-binding protein 2 |
| P17936 | Insulin-like growth factor-binding protein 3 |
| P35858 | Insulin-like growth factor-binding protein complex acid labile subunit |
| P35858 | Insulin-like growth factor-binding protein complex acid labile subunit |
| P19827 | Inter-alpha-trypsin inhibitor heavy chain H1 |
| P19823 | Inter-alpha-trypsin inhibitor heavy chain H2 |
| Q14624 | Inter-alpha-trypsin inhibitor heavy chain H4 |
| P05362 | Intercellular adhesion molecule 1 |
| P22301 | Interleukin-10 |
| P05231 | Interleukin-6 |
| P03956 | Interstitial collagenase |
| P29622 | Kallistatin |
| P13645 | Keratin type I cytoskeletal 10 |
| P35527 | Keratin type I cytoskeletal 9 |
| P35908 | Keratin-type II cytoskeletal 2 epidermal |
| P01042 | Kininogen-1 |
| P02788 | Lactotransferrin |
| P02750 | Leucine-rich alpha-2-glycoprotein |
| P18428 | Lipopolysaccharide-binding protein |
| P14151 | L-selectin |
| P51884 | Lumican |
| P61626 | Lysozyme C |
| P48740 | Mannan-binding lectin serine protease 1 |
| O00187 | Mannan-binding lectin serine protease 2 |
| P11226 | Mannose-binding protein C |

TABLE 1-continued

Example human blood plasma proteins for detection

| Accession Number | UniProt Protein Name |
|---|---|
| P08493 | Matrix Gla protein |
| P14780 | Matrix metalloproteinase-9 |
| P08582 | Melanotransferrin |
| P01033 | Metalloproteinase inhibitor 1 |
| P16035 | Metalloproteinase inhibitor 2 |
| Q99727 | Metalloproteinase inhibitor 4 |
| P10636 | Microtubule-associated protein tau |
| Q8WXI7 | Mucin-16 |
| P02686 | Myelin basic protein |
| P24158 | Myeloblastin |
| P05164 | Myeloperoxidase |
| O94760 | N(G) N(G)-dimethylarginine dimethylamino-hydrolase 1 |
| Q96PD5 | N-acetylmuramoyl-L-alanine amidase |
| P16860 | Natriuretic peptides B |
| O60462 | Neuropilin-2 |
| P80188 | Neutrophil gelatinase-associated lipocalin |
| Q16625 | Occludin |
| P10451 | Osteopontin |
| P78380 | Oxidized low-density lipoprotein receptor 1 |
| Q13219 | Pappalysin-1 |
| Q06830 | Peroxiredoxin-1 |
| P32119 | Peroxiredoxin-2 |
| P04180 | Phosphatidylcholine-sterol acyltransferase |
| P80108 | Phosphatidylinositol-glycan-specific phospholipase D |
| P55058 | Phospholipid transfer protein |
| P36955 | Pigment epithelium-derived factor |
| P05155 | Plasma protease C1 inhibitor |
| P05154 | Plasma serine protease inhibitor |
| P00747 | Plasminogen |
| P05121 | Plasminogen activator inhibitor 1 |
| P13796 | Plastin-2 |
| P16284 | Platelet endothelial cell adhesion molecule |
| Q9HCN6 | Platelet glycoprotein VI |
| Q13093 | Platelet-activating factor acetylhydrolase |
| P20742 | Pregnancy zone protein |
| Q8IZF2 | Probable G-protein coupled receptor |
| P01210 | Proenkephalin-A |
| P01236 | Prolactin |
| P02760 | Protein AMBP |
| Q99497 | Protein DJ-1 |
| P80511 | Protein S100-A12 |
| P06702 | Protein S100-A9 |
| P04271 | Protein S100-B |
| Q9UK55 | Protein Z-dependent protease inhibitor |
| Q92954 | Proteoglycan 4 |
| P00734 | Prothrombin |
| P16109 | P-selectin |
| Q9UJF2 | Ras GTPase-activating protein nGAP |
| Q9HD89 | Resistin |
| P02753 | Retinol-binding protein 4 |
| P02787 | Serotransferrin |
| P02768 | Serum albumin |
| P0DJ18\|P0DJI9 | Serum amyloid A-1 protein |
| P35542 | Serum amyloid A-4 protein |
| P02743 | Serum amyloid P-component |
| P27169 | Serum paraoxonase/arylesterase 1 |
| Q15166 | Serum paraoxonase/lactonase 3 |
| P04278 | Sex hormone-binding globulin |
| P09486 | SPARC |
| Q9NWM0 | Spermine oxidase |
| Q8IVG5 | Sterile alpha motif domain-containing protein 9-like |
| P08254 | Stromelysin-1 |
| Q7Z7G0 | Target of Nesh-SH3 |
| Q9BXI6 | TBC1 domain family member 10A |
| P24821 | Tenascin |
| P22105\|Q16473 | Tenascin-X |
| P05452 | Tetranectin |
| P07204 | Thrombomodulin |
| P07996 | Thrombospondin-1 |
| P35443 | Thrombospondin-4 |
| P01266 | Thyroglobulin |
| P05543 | Thyroxine-binding globulin |
| P10646 | Tissue factor pathway inhibitor (isoform 1) |
| P00750 | Tissue-type plasminogen activator |
| P35716 | Transcription factor SOX-11 |
| P02786 | Transferrin receptor protein 1 |
| P02766 | Transthyretin |
| P19438 | Tumor necrosis factor receptor 1A |
| P20333 | Tumor necrosis factor receptor 1B |
| P19438 | Tumor necrosis factor receptor superfamily member 1A |
| P19320 | Vascular cell adhesion protein 1 |
| P49765 | Vascular endothelial growth factor |
| O43915 | Vascular endothelial growth factor D |
| Q9NY84 | Vascular non-inflammatory molecule 3 |
| Q6EMK4 | Vasorin |
| P02774 | Vitamin D-binding protein |
| P04070 | Vitamin K-dependent protein C |
| P07225 | Vitamin K-dependent protein S |
| P22891 | Vitamin K-dependent protein Z |
| P22891 | Vitamin K-dependent protein Z variant 1 |
| P04004 | Vitronectin |
| P04275 | von Willebrand factor |
| P12955 | Xaa-Pro dipeptidase |
| P25311 | Zinc-alpha-2-glycoprotein |

Stable Isotope Labelled Molecules

The disclosed methods can utilize any label that produces two stable isotope labelled standard (SIS) molecules of distinguishable mass. The molecules to be labeled can be selected from those molecules expected to be present in the test sample in their unlabeled form, e.g., a target molecule. However, it should be understood that the SIS molecules do not have to be present in the test sample, or in the control sample, in unlabeled form. An SIS standard may be any molecule that can be modified to incorporate one or more stable isotopes, e.g., $^{2}H$, $^{13}C$, $^{15}N$, $^{18}O$, or $^{34}S$. A SIS molecule may have a mass-to-charge ratio range of about positive, or negative, 1-5000 m/z, about 1-4000 m/z, about 1-3000 m/z, about 1-2000 m/z, about 1-1000 m/z, etc.

In embodiments, two stable isotope labelled standard (SIS) molecules do not need to have distinguishable masses if the labelled molecules can be fragmented and the mass of the mass of the fragments can be distinguished.

Any combination of stable isotope labeling that creates two SIS molecules of distinguishable masses is acceptable. In embodiments, a first SIS comprises a single stable isotope label and a second SIS comprises two stable isotope labels. In embodiments, a stable isotope may be selected from $^{2}H$, $^{13}C$, $^{15}N$, $^{18}O$, $^{34}S$ or combinations thereof.

In embodiments, a peptide SIS or protein SIS is stable isotope labelled at a terminus, e.g., an N-, or C-terminus, or both. In embodiments, a peptide SIS or protein SIS is stable isotope labelled at one or more internal or terminal amino acids, or combinations thereof.

In some embodiments, a peptide SIS or protein SIS is labelled both at a terminus, e.g., an N-, or C-terminus (or both) and at one or more internal amino acids. In embodiments, a peptide SIS or protein SIS is labelled with a single stable isotope at a single amino acid. In embodiments, a peptide SIS or protein SIS is labelled with at least two stable isotopes (which may be the same or different stable isotopes) at a single amino acid. In embodiments, a peptide SIS or protein SIS is labelled with a single stable isotope at a two different amino acids.

In some embodiments, a digested peptide is labelled at the n- or c-terminus. In some embodiments, a tryptic peptide is labeled at a c-terminal lysine or arginine. In some embodiments, a peptide produced by chymotrypsin digestion is labeled at a c-terminal Tyr, Phe, Trp, Leu or Met. In some embodiments, a peptide produced by digestion with LysN or LysC is labeled at a c-terminal lysine. In some embodiments, a peptide produced by digestion with Glu-C is labeled at a c-terminal glutamine. In some embodiments, a peptide produced by digestion with Asp-N is labeled at a c-terminal asparagine. In some embodiments, a peptide produced by digestion with ArgC is labeled at a c-terminal arginine. In some embodiments, peptides resulting from digestion by different enzymes, with varied cut site preferences, can be assayed in a single multiplexed assay.

The disclosed methods utilized two stable isotope labeled molecules for each set of standards. It should be understood that any number of paired SIS molecules may be utilized in a multiplexed assay. For example, a first and second SIS molecules for each of 1, 2, 3, 4, 5, 6, 7, 8, 9, 10, 15, 20, 25, 30, 35, 40, 45, 50, 55, 60, 65, 70, 75, 80, 85, 90, 95, 100 or more target molecules may be assayed simultaneously.

Detection of Target Molecules

The methods disclosed herein can utilized any method of distinguishing masses of target molecules and stable isotope labelled standard molecules. In particular, methods of the present invention utilized mass spectrometry. The present methods are applicable to any type of mass spectrometry including those paired with gas or liquid chromatography, electrospray ionization (ESI), atmospheric pressure chemical ionization (APCI), electron impact ionization (EI). Specific types of mass spectrometry include, Matrix Assisted Laser Desorption Ionisation (MALDI)/TOF, Surface Enhanced Laser Desorption Ionization (SELDI)/TOF, tandem mass spectrometry, Thermal Ionization Mass Spectrometry (TIMS), Spark Source Mass Spectrometry (SSMS), time-of-flight (TOF), quadrupole (Q), ion trap (IT), orbitrap, ion cyclotron resonance (ICR), magnetic sector and any tandem mass spec (e.g., a combination of two or more of the above mass analyzers such as triple quadrupole (QqQ)), Q-TOF, Q-IT, TOF-TOF, Q-orbitrap, or others. A mass spectrometer used for the disclosed methods may have a mass-to-charge ratio detection range of about 0-5000 m/z, about 0-4000 m/z, about 0-3000 m/z, about 0-2000 m/z, about 0-1000 m/z, etc. in a positive or negative mode.

Example 1

Materials and Methods

This example provides the materials and methods used to obtain the results provided in the Examples below.

Materials $^{13}C/^{15}N$-labeled lysine and arginine (>99% isotopic purity) were purchased from Cambridge Isotope Laboratories (Tewksbury, Mass., USA). $^{13}C/^{15}N$-labeled phenylalanine and leucine, and all unlabeled amino acids, were from Sigma-Aldrich (Oakville, Ontario, Canada), as well as LC-MS grade methanol, acetonitrile and water, formic acid, Tris base, phosphate buffered saline (10× concentrated), dimethylformamide (DMF), bovine serum albumin (BSA), urea, dithiothreitol (DTT) and iodoacetamide. Human plasma and chicken plasma were from Bioreclamation IVT (Baltimore, Md., USA). TPCK-treated trypsin was from Worthington (Lakewood, N.J., USA).

Standard Peptides

Thirty-one surrogate peptides with varying hydrophobicities and varying endogenous concentrations were chosen from human plasma proteins using the PeptideTracker database.[19] The sequences of all peptides were selected to be appropriate for use in MRM-based assays based on several criteria[20]. Peptides were synthesized and characterized in-house via Fmoc chemistry according to previously published methods.[21] Briefly, these $^{13}C/^{15}N$-labeled tryptic peptides were purified by RP-HPLC and characterized by MALDI-TOF-MS and capillary zone electrophoresis with UV detection. The peptides were outsourced for amino acid analysis (AAA) (Performed by AAA Service Laboratory, Inc., Damascus, Oreg.). Two different labeled versions of the chosen peptides were synthesized: one with a labeled C-terminus lysine or arginine (Stable Isotope Standard; SIS 1) and another with an internal $^{13}C/^{15}N$-labeled phenylalanine or leucine in addition to the C-terminal labeled amino acid (SIS 2).

Sample Processing

The following steps were performed by the Tecan Evo™ (Männedorf, Switzerland) liquid handling robot. First, raw pooled normal human plasma (10 µL) or 4 surrogate matrices (chicken plasma, dimethylated human plasma digest, phosphate buffered saline (PBS) and BSA solution (10 mg/mL in PBS)) were denatured and reduced with 20 µL 9M urea/20 mM dithiothreitol for 30 minutes at 37° C. The alkylation step was then performed by adding 104, iodoacetamide solution (160 mM) and further incubated at 37° C. for 30 minutes in the dark. The samples were diluted with 300 µL TRIS buffer (100 mM) prior to the addition of 354, of trypsin solution (1 µg/µL) for overnight digestion at 37° C. The amount of trypsin in the digest was calculated for a 1:20 enzyme to substrate ratio in normal human plasma (considered to be 70 µg/mL). Digests were then acidified with 50 µL of formic acid (10%), and 37.5 µg of protein (22.8 µL of the acidified digest) was transferred and combined with 12.7 µL of solutions containing varying SIS peptide concentrations, depending on the sample concentration. Samples were then diluted with 0.1% formic acid in order to reduce the concentration of acetonitrile to <1%, and finally concentrated by solid phase extraction (SPE) using a mixed-mode reversed phase cartridge (Waters Oasis HLB 96 well plates, 30 µm, Mississauga, Ontario). Samples were lyophilized and rehydrated in 37.5 µL of 0.1% formic acid prior to injection, to give a final plasma protein concentration of 1 µg/µL.

For the dimethylated human plasma, reductive methylation of amines was performed according to literature[22] immediately after digestion. Briefly, digests underwent solid phase extraction to remove remaining urea buffer and lyophilization. Dried digests were resuspended in 100 mM TEAB buffer and all primary amines in the human plasma digest were reductively dimethylated using formaldehyde and sodium cyanoborohydride, shifting the masses of all endogenous peptides in order to create a human plasma-based blank matrix. SIS peptide mixtures were added after the reductive methylation reaction, and before the SPE step.

Calibration Curves and SIS Peptide Mixtures

To determine the concentration ranges for each peptide, an equimolar mixture of all 31 peptides was prepared. An eleven point dilution curve containing SIS 1 and SIS 2 peptides were spiked into human plasma digest (from 0.1 fmol to 20000 fmol per 15 µg of human plasma protein) in order to obtain a rough estimate of the lower limit of quantitation (LLOQ) for the assays (based on the signal-to-noise ratios (S/N) of both SIS peptides in the dilution curve). The target S/N ratio for the LLOQ was approximately 10 to 1. The endogenous peptide levels were also estimated using the closest SIS peptide concentration in the dilution curve in order to ensure that the endogenous levels were included within the concentration range of the calibration curve. The calibration curves for all peptides were designed as illustrated in scheme 1, so that the same SIS peptide stock solutions could be used for all of the samples. The concentration ranges were determined based on the estimated LLOQ and the estimated endogenous levels. If the endogenous levels were high, the LLOQ concentration was shifted upward for the final assay so that the endogenous levels would fall near the middle of the range.

Mixed stock solutions of all SIS 1 and SIS 2 peptides were prepared, each at a concentration two times higher than the ULOQ. These stock solutions were diluted at appropriate amounts and spiked into human plasma to prepare the calibration curve and QC samples. All peptide dilutions (in 30% acetonitrile containing 1% formic acid) were performed by the Tecan Evo™ in Eppendorf™ LoBind Microcentrifuge tubes (Mississauga, Ontario), immediately prior to spiking. Each calibration curve (in each matrix types) consisted of standards B to J, prepared in singlicate (except for a duplicate standard B). Six QC samples at 3 concentration levels were prepared in human plasma digest.

LC-MS/MS

Digested samples (15 µL) were separated by reversed phase on an Agilent 1290 Infinity UHPLC system (G4220A) that included and autosampler (G4226A), column heater (G1316C) and degasser (G1330B). The separation was carried out using an Agilent Zorbax Eclipse (2.1 mm ID×150 mm long, 1.8 µm) column, maintained at 50° C. Mobile phases A and B consisted of water and acetonitrile, respectively, both containing 0.1% formic acid. The flow rate was 0.4 mL/min throughout the following 30 min multi-step gradient: 0 min: 2.7% B, 2 min: 9.9% B, 15 min: 17.1% B 22 min: 26.10% B, 25 min: 40.50% B, 27 min, 81.0% B, 29 min: 81.0% B, 30 min: 2.7% B. The UHPLC system was interfaced to an Agilent 6490 triple quadrupole mass spectrometer via a standard-flow ESI source. The capillary and nozzle voltages were set at 3500V and 300V, respectively. The sheath gas was set at 11 L/min at a temperature of 250° C., and the drying gas was set as a flow rate of 15 L/min and a temperature of 150° C. The nebulizer gas was set at 30 psi, and both Q1 and Q3 were set to unit resolution.

Data was acquired in the positive dynamic MRM mode within 1.0-minute retention-time windows, using a cycle time of 900 ms for a minimum dwell time of 13.4 ms. The equivalent 5 optimized transitions were used to monitor all three isotopes of each peptide: light (endogenous) peptide, SIS 1 and SIS 2 (see Supporting Information for the transition list). The system was controlled by Agilent's MassHunter software (version B.07.00 Build 7.0.7022.0).

Data Processing

The raw data was processed and the integration was performed by Skyline software [23] version 3.5. Quantitation was performed via regression analysis of peptide standard curves (1/x weighting), constructed from all transitions that were found to be interference free and detectable across the entire concentration range. All standard and QC samples contained a constant amount of internal standard (SIS 1) and a variable amount of SIS 2 peptide. The concentration of the SIS 2 peptide in each of the QC samples (n=6, at 3 levels in human plasma) were calculated using the 4 different calibration strategies (using different isotope ratios to construct the standard curve), and the performances of the calibration strategies were compared. Intra-day and inter-day (2) precision and accuracy were assessed.

Example 2

Assay Development

Even though the peptides had been used in previous assays, these assays were developed again to avoid any potential bias. The peptides selected were suitable for MRM assays and they each contained phenylalanine and leucine near the C-terminal in order to facilitate synthesis of a doubly labeled peptide. The 31 peptides represent a spread in hydrophobicity, sequence length, and endogenous protein concentration in human plasma (FIG. 1).

First, assay concentration ranges were established by running dilution curves of the SIS peptides in a human plasma digest. The lower limits of quantitation (LLOQ) were estimated based on S/N ratios in human plasma (approx. 10× S/N), and the endogenous concentration levels were also estimated using the dilution curve. The final assay concentration ranges were established based on these LLOQ values (which spanned a 2000-fold range) and, if needed, were adjusted upward so that the endogenous concentrations would be close to the middle of the range. Table 2 shows the list of peptides used in this study. The final LLOQs for all peptides lie between 0.5 and 25 fmol, on column.

TABLE 2

List of peptides synthesized. For the doubly labeled peptides, the second labeled amino acid is indicated with an asterix ($^{13}C/^{15}N$ Phe or Leu).

| Peptide | SEQ ID NO: | Protein | UniProt Acc. No. | Internally Labeled Peptide (L or F*) | LLOQ (fmol/ column) | ULOQ (fmol/ column) | RT (min) |
|---|---|---|---|---|---|---|---|
| AEIEYLEK | 1 | L-selectin | P14151 | AEIEYL*EK | 2.5 | 5000 | 14.9 |
| AFLLTPR | 2 | Apolipoprotein M | O95445 | AFLL*TPR | 1.5 | 3000 | 22.9 |
| AGYVLHR | 3 | Mannan-binding lectin serine protease 2 | O00187 | AGYVL*HR | 3.0 | 6000 | 5.8 |
| ATAVVDGAFK | 4 | Peroxiredoxin-2 | P32119 | ATAVVDGAF*K | 7.5 | 15000 | 14.8 |
| AVGLAGTFR | 5 | Collagen alpha-1(XVIII) chain | P39060 | AVGLAGTF*R | 1.0 | 2000 | 17.5 |
| AVYEAVLR | 6 | Xaa-Pro dipeptidase | P12955 | AVYEAVL*R | 1.5 | 3000 | 16.2 |

TABLE 2-continued

List of peptides synthesized. For the doubly labeled peptides, the second labeled amino acid is indicated with an asterix ($^{13}C/^{15}N$ Phe or Leu).

| Peptide | SEQ ID NO: | Protein | UniProt Acc. No. | Internally Labeled Peptide (L or F*) | LLOQ (fmol/ column) | ULOQ (fmol/ column) | RT (min) |
|---|---|---|---|---|---|---|---|
| DGAGDVAFVK | 7 | Serotransferrin | P02787 | DGAGDVAF*VK | 25.0 | 50000 | 14.8 |
| EGYYGYTGAFR | 8 | Serotransferrin | P02787 | EGYYGYTGAF*R | 10.0 | 20000 | 21.3 |
| ESDTSYVSLK | 9 | C-reactive protein | P02741 | ESDTSYVSL*K | 4.5 | 9000 | 13.0 |
| ETLLQDFR | 10 | Protein AMBP | P02760 | ETLLQDF*R | 2.5 | 5000 | 25.5 |
| FLNVLSPR | 11 | Insulin-like growth factor-binding protein 3 | P17936 | FLNVL*SPR | 2.5 | 5000 | 25.8 |
| GVASLFAGR | 12 | Cartilage acidic protein 1 | Q9NQ79 | GVASLF*AGR | 1.25 | 2500 | 22.0 |
| GVTFLLR | 13 | Alpha-1B-glycoprotein | P04217 | GVTF*LLR | 2.5 | 5000 | 25.6 |
| HLVALSPK | 14 | Corticosteroid-binding globulin | P08185 | HLVAL*SPK | 12.5 | 25000 | 9.4 |
| IALDFQR | 15 | Galectin-3 | P17931 | IALDF*QR | 4.0 | 8000 | 20.2 |
| IANVFTNAFR | 16 | Myeloperoxidase | P05164 | IANVFTNAF*R | 2.5 | 5000 | 28.0 |
| ITLPDFTGDLR | 17 | Lipopolysaccharide-binding protein | P18428 | ITLPDFTGDL*R | 8.0 | 16000 | 34.1 |
| LVGGLHR | 18 | CD5 antigen-like | O43866 | LVGGL*HR | 5.0 | 10000 | 5.4 |
| NFPSPVDAAFR | 19 | Hemopexin | P02790 | NFPSPVDAAF*R | 2.0 | 4000 | 28.0 |
| SALVLQYLR | 20 | Coagulation factor IX | P00740 | SALVLQYL*R | 1.3 | 2500 | 30.5 |
| TGAQELLR | 21 | Gelsolin | P06396 | TGAQELL*R | 8.0 | 16000 | 11.5 |
| TGISPLALIK | 22 | Apolipoprotein B-100 | P04114 | TGISPLAL*IK | 1.5 | 3000 | 32.9 |
| TGIVSGFGR | 23 | Coagulation factor X | P00742 | TGIVSGF*GR | 1.5 | 3000 | 16.2 |
| TLAFPLTIR | 24 | Endothelial protein C receptor | Q9UNN8 | TLAFPL*TIR | 0.5 | 1000 | 34.0 |
| TLEAQLTPR | 25 | Heparin cofactor 2 | P05546 | TLEAQL*TPR | 3.0 | 6000 | 14.6 |
| TSDQIHFFFAK | 26 | Antithrombin-III | P01008 | TSDQIHFFF*AK | 4.0 | 8000 | 28.5 |
| TVGSDTFYSFK | 27 | Kininogen-1 | P01042 | TVGSDTFYSF*K | 3.0 | 6000 | 23.5 |
| VAQELEEK | 28 | Apolipoprotein L1 | O14791 | VAQEL*EEK | 10.0 | 20000 | 4.6 |
| VVEESELAR | 29 | Complement component C9 | P02748 | VVEESEL*AR | 1.0 | 2000 | 8.4 |
| VVLGDQDLK | 30 | Hyaluronan-binding protein 2 | Q14520 | VVLGDQDL*K | 1.0 | 2000 | 14.3 |

TABLE 2-continued

List of peptides synthesized. For the doubly labeled peptides, the second labeled amino acid is indicated with an asterix ($^{13}C/^{15}N$ Phe or Leu).

| Peptide | SEQ ID NO: | Protein | UniProt Acc. No. | Internally Labeled Peptide (L or F*) | LLOQ (fmol/ column) | ULOQ (fmol/ column) | RT (min) |
|---|---|---|---|---|---|---|---|
| VYFAGFPR | 31 | Vitamin K-dependent protein S | P07225 | VYFAGF*PR | 3.0 | 6000 | 26.2 |

Example 3

Double-SIS-Peptide Assay

Figure 2:
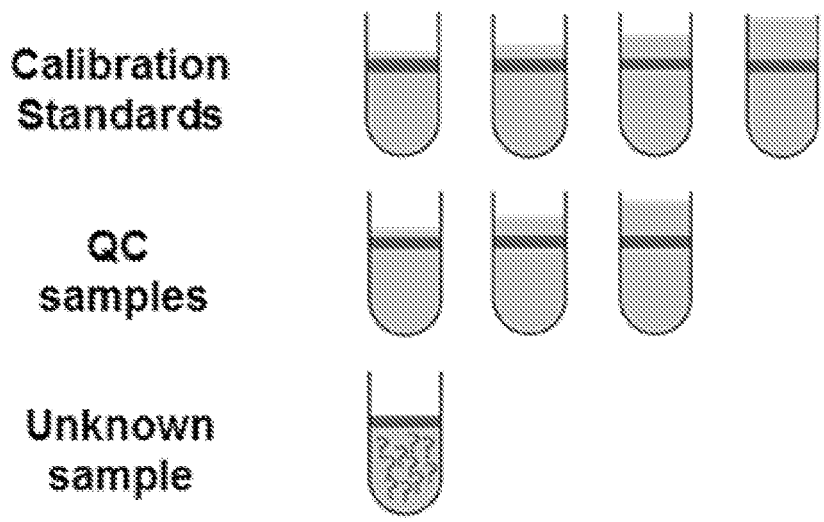
FIG. 2 is a schematic drawing outlining the disclosed double-SIS-peptide calibration method

To evaluate the performance of the double-SIS-peptide strategy, two batches were extracted on separate days from new sets of SIS peptide dilutions prepared from scratch. QC samples prepared in human plasma were used to evaluate the precision and the accuracy of the entire protocol. Six replicates of QC samples prepared at three different SIS-2 concentration levels spanning the entire 2000 fold range were evaluated each day. Both the standard curve and the QC samples were calculated using the SIS-2/SIS-1 area ratio. In this method, an unknown sample would be calculated using the light/SIS-1 ratio (see FIG. 2). Table 3 shows the curve parameters and the precision and accuracy results for the double-SIS-peptide calibration method for all peptides. The analytical performance of the double-SIS-peptide strategy was excellent—the coefficients of variation (CVs) for each QC sample for all peptides were all ≤12.1% and the accuracies were all between 90.0% and 105.3%. All 31 peptides easily met the precision and accuracy criteria set by the FDA guidelines for bioanalytical method validation[8] when the experiment was repeated on different days, proving the merits of this approach.

TABLE 3

Curve parameters and QC statistics for all peptides for double-SIS method. QC samples (n = 12/level, over all experiments) and calibration curve in human P1.

| Peptide | SEQ ID NO: | Curve parameters (LOQs in pmol/ml plasma) | | | | Low QC | | Mid QC | | High QC | |
|---|---|---|---|---|---|---|---|---|---|---|---|
| | | LLOQ | ULOQ | Avg. Slope (x $10^{-2}$) | Avg. Intercept (x $10^{-3}$) | % Accur. | % CV | % Accur. | % CV | % Accur. | % CV |
| AEIEYLEK | 1 | 11.7 | 23333 | 1.01 | -2.98 | 95.8 | 10.2 | 98.1 | 9.4 | 104.1 | 10.7 |
| AFLLTPR | 2 | 7.0 | 14000 | 1.10 | -4.32 | 96.0 | 7.7 | 95.2 | 4.5 | 99.4 | 6.9 |
| AGYVLHR | 3 | 14.0 | 28000 | 1.36 | -4.29 | 103.0 | 8.9 | 99.5 | 5.3 | 102.9 | 5.7 |
| ATAVVDGAFK | 4 | 35.0 | 70000 | 1.26 | -5.10 | 93.0 | 9.6 | 90.0 | 7.5 | 96.7 | 5.7 |
| AVGLAGTFR | 5 | 4.7 | 9333 | 1.15 | -5.13 | 101.0 | 6.8 | 94.1 | 8.0 | 99.9 | 6.2 |
| AVYEAVLR | 6 | 7.0 | 14000 | 1.23 | -5.38 | 96.6 | 6.3 | 94.8 | 6.6 | 102.4 | 8.0 |
| DGAGDVAFVK | 7 | 116.7 | 233333 | 1.01 | -0.77 | 95.8 | 9.3 | 102.4 | 7.3 | 99.9 | 6.6 |
| EGYYGYTGAFR | 8 | 46.7 | 93333 | 1.24 | -4.75 | 98.7 | 8.5 | 94.8 | 6.9 | 100.2 | 4.5 |
| ESDTSYVSLK | 9 | 21.0 | 42000 | 1.59 | -1.34 | 101.5 | 9.0 | 92.5 | 8.7 | 101.3 | 5.8 |
| ETLLQDFR | 10 | 11.7 | 23333 | 1.12 | -3.14 | 96.7 | 9.7 | 97.5 | 8.0 | 103.4 | 5.4 |
| FLNVLSPR | 11 | 11.7 | 23333 | 1.09 | -5.04 | 95.6 | 6.6 | 92.8 | 5.9 | 100.2 | 3.9 |
| GVASLFAGR | 12 | 5.8 | 11667 | 1.11 | -3.75 | 95.7 | 6.2 | 96.1 | 4.8 | 100.9 | 5.4 |
| GVTFLLR | 13 | 11.7 | 23333 | 1.15 | -3.92 | 94.8 | 7.0 | 95.8 | 6.2 | 100.8 | 3.9 |
| HLVALSPK | 14 | 58.3 | 116667 | 1.08 | -5.03 | 97.5 | 8.7 | 91.5 | 9.2 | 95.2 | 6.5 |
| IALDFQR | 15 | 18.7 | 37333 | 1.10 | -4.85 | 98.2 | 4.9 | 94.2 | 4.6 | 100.1 | 3.3 |

TABLE 3-continued

Curve parameters and QC statistics for all peptides for double-SIS method. QC samples
(n = 12/level, over all experiments) and calibration curve in human P1.

| Peptide | SEQ ID NO: | Curve parameters (LOQs in pmol/ml plasma) | | | | Low QC | | Mid QC | | High QC | |
|---|---|---|---|---|---|---|---|---|---|---|---|
| | | LLOQ | ULOQ | Avg. Slope (x $10^{-2}$) | Avg. Intercept (x $10^{-3}$) | % Accur. | % CV | % Accur. | % CV | % Accur. | % CV |
| IANVFTNAFR | 16 | 11.7 | 23333 | 1.25 | −3.42 | 98.2 | 6.6 | 93.4 | 6.8 | 100.6 | 6.7 |
| ITLPDFTGDLR | 17 | 37.3 | 74667 | 1.02 | 1.63 | 99.5 | 10.0 | 112.4 | 8.1 | 96.8 | 5.9 |
| LVGGLHR | 18 | 23.3 | 46667 | 1.10 | 0.31 | 92.3 | 8.4 | 92.5 | 9.0 | 102.8 | 5.7 |
| NFPSPVDAAFR | 19 | 9.3 | 18667 | 1.31 | −4.73 | 97.4 | 5.0 | 96.7 | 7.1 | 100.3 | 4.7 |
| SALVLQYLR | 20 | 5.8 | 11667 | 1.33 | −4.37 | 94.6 | 7.5 | 93.2 | 8.0 | 101.4 | 5.3 |
| TGAQELLR | 21 | 37.3 | 74667 | 1.04 | −3.30 | 97.4 | 7.0 | 94.8 | 7.0 | 101.0 | 4.0 |
| TGISPLALIK | 22 | 7.0 | 14000 | 1.12 | −3.23 | 96.4 | 10.0 | 97.3 | 9.4 | 102.2 | 6.9 |
| TGIVSGFGR | 23 | 7.0 | 14000 | 1.20 | −4.66 | 97.8 | 5.8 | 96.2 | 6.1 | 103.1 | 5.4 |
| TLAFPLTIR | 24 | 2.3 | 4667 | 1.04 | −3.11 | 99.9 | 9.7 | 94.6 | 7.7 | 97.0 | 8.1 |
| TLEAQLTPR | 25 | 14.0 | 28000 | 1.01 | −2.59 | 105.1 | 10.4 | 101.4 | 9.5 | 105.5 | 10.2 |
| TSDQIHFFFAK | 26 | 18.7 | 37333 | 1.10 | −4.15 | 100.6 | 8.5 | 97.7 | 7.1 | 99.8 | 4.5 |
| TVGSDTFYSFK | 27 | 14.0 | 28000 | 1.24 | −4.72 | 101.7 | 12.1 | 93.5 | 5.5 | 98.6 | 7.5 |
| VAQELEEK | 28 | 46.7 | 93333 | 1.18 | −3.86 | 98.9 | 8.6 | 99.3 | 3.6 | 103.0 | 4.4 |
| VVEESELAR | 29 | 4.7 | 9333 | 1.03 | −4.74 | 98.9 | 11.2 | 91.4 | 7.8 | 100.3 | 8.5 |
| VVLGDQDLK | 30 | 4.7 | 9333 | 1.16 | −3.42 | 91.4 | 9.0 | 96.2 | 10.5 | 105.3 | 10.6 |
| VYFAGFPR | 31 | 14.0 | 28000 | 0.86 | −2.08 | 98.3 | 10.1 | 96.3 | 9.5 | 102.7 | 6.5 |
| Average | | — | — | — | — | 97.7 | 8.4 | 96.0 | 7.3 | 100.9 | 6.2 |

Example 4

Evaluation of Calibration Strategies

Traditional calibration methods were compared to the new methods disclosed herein, using two different stable isotope-labeled standard (SIS) peptides for each endogenous peptide to be quantified, enabling an external calibration curve as well as the quality control samples to be prepared in pooled human plasma without interference from endogenous peptides. This strategy enables the determination of the accuracy of the assay, which can facilitate method development and validation.

Having two SIS-peptide standards provides a flawless way to evaluate the performance of the different commonly used calibration strategies for multiplexed protein assays and compare with the two SIS peptide method. Using the same QC samples, prepared with known concentrations of (SIS 2) peptide in human plasma, at three different concentration levels, the concentrations of SIS-2 in these samples, were measured without interference from endogenous peptides, and using different calibration methods.

A commonly used calibration strategy is the reverse curve. This strategy consists of building a calibration curve from various SIS-peptide concentrations spiked into pooled human plasma, using the endogenous plasma levels as internal standards to normalize the signal. The calibration curve is then plotted as the area ratio between the SIS peptide and the endogenous (or light) peptide versus the concentration of SIS peptide. To calculate the concentration of endogenous peptide in unknown samples, known concentrations of SIS peptides are added to the unknown sample and the reverse ratio (light/SIS peptide area ratio) is used to calculate the concentration of light peptide in the unknown sample. In order for this "flipping" to function properly, some kind of correction needs to be applied. If the concentration of SIS peptide added to unknown samples is "balanced" to approximate the concentration of endogenous peptide in the matrix used to construct the calibration curve, the reverse ratio measured in the unknown sample can be directly read off the calibration curve.

An alternative is to apply a correction factor. Also, a fixed amount of light standard peptide can be added to the calibration curve in order to increase and improve the reproducibility of the light peptide signal in the standard curve samples. In either case, accuracy bias can be introduced. This strategy does have the benefit of using an external calibration curve in an appropriate matrix and maintains the use of an internal standard to normalize for fluctuations in analyte response. Consequently, these reverse curve measurements can be very reproducible and are excellent for comparing concentrations of protein between samples within an experiment.

Figure 3A:
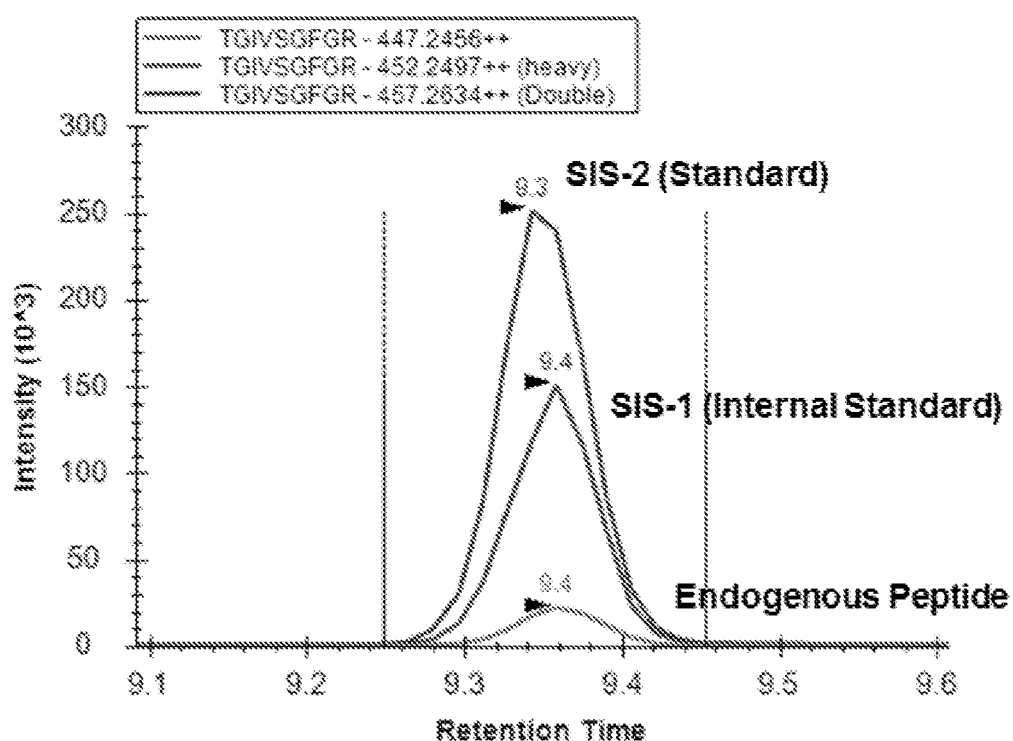
FIG. 3A is an illustration of the different isotopes monitored (native, single-labeled, and double labeled TGIVSGFGR; SEQ ID NO: 23) in a Mid QC sample using the double SIS method. A mid QC sample is a quality control sample (which is independent from control samples used in developing the calibration curve) which contains a concentration of calibration standard (double labeled SIS, indicated as SIS-2) approximating the middle of the calibration curve (see FIG. 6, mid QC).
Figure 3B:
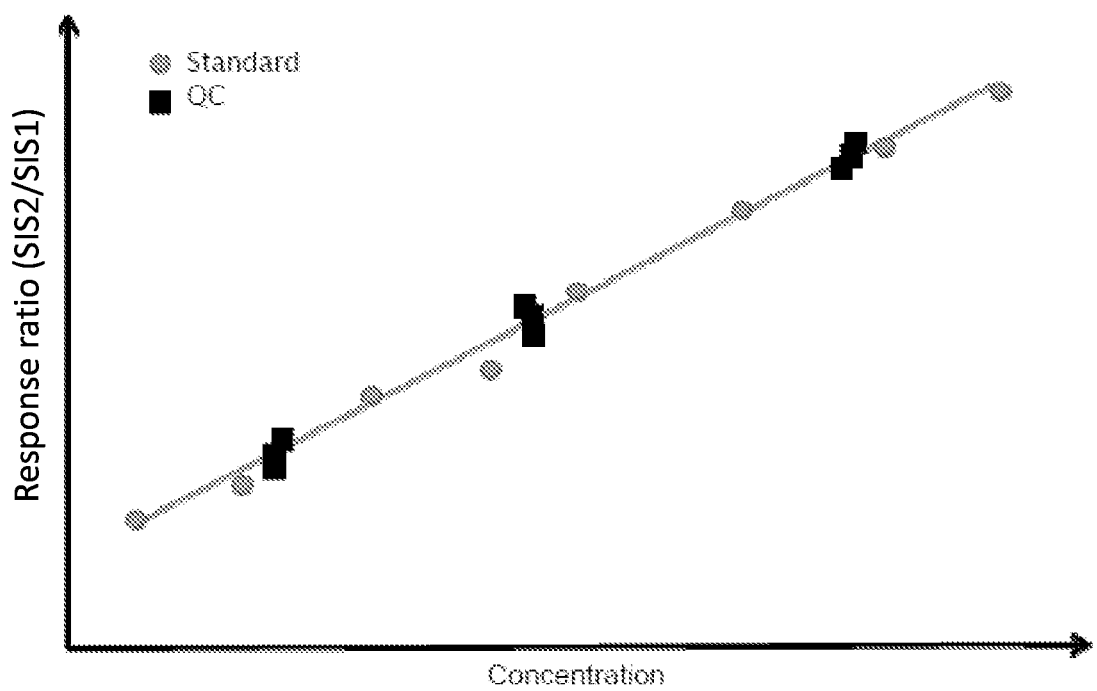
FIG. 3B is an exemplary calibration curve generated by plotting the response ratio (e.g., using a response such as an area under a curve as shown in FIG. 3A) of a calibration standard to an internal standard against the known concentration of the calibration standard. This response ratio is plotted for each concentration of calibration standard used in the assay and a best fit line plotted to the data points generating a calibration curve. Quality control (QC) samples can be generated independently of the calibration samples using a number of distinct concentrations of calibration standard and the same uniform concentration of internal standard. Quality control samples provide an independent verification of the accuracy of the calibration curve.

The main difference between reverse curves and the double-SIS-peptide method is that the identity of the internal standard is different between the standard curve and the unknown samples for reverse curves, while the internal standard is the same (and added equally) for all sample types in the double-SIS-peptide method. The accuracy of two types of reverse curves was evaluated. Curves using the endogenous (light) peptide levels to normalize the signal for both the standard and QC samples (since we are quantifying the SIS-2 peptide) were calculated and the concentrations of a second set of QC samples calculated using a "balanced" level of SIS-1 peptide (evaluated using a different set of QC samples since the original set of QC samples contain a fixed concentration of SIS-1 peptide as internal standard). FIG. 3 illustrates the differences between isotopes monitored in a typical QC sample for the double-SIS-peptide method.

The use of SIS peptides in the single-point calibration method was also evaluated. Single-point calibration consists of calculating the ratio between a known amount of SIS peptide and the analyte. The analyte/SIS peptide ratio is then multiplied by the concentration of the SIS peptide spiked in the sample. This calibration method assumes that the calibration curve in the range that includes the concentration of the SIS peptide and the analyte is linear, has a slope of 1 and that the intercept goes through the origin. These assumptions do not significantly affect the results when the SIS peptide concentration is very close to the analyte concentration, but will be less accurate the further apart these concentrations are. In the experiment, the concentrations of the SIS-2 peptide in the QC samples were calculated using the SIS 1 peptide (internal standard) that was added to all QC samples.

Figure 4:
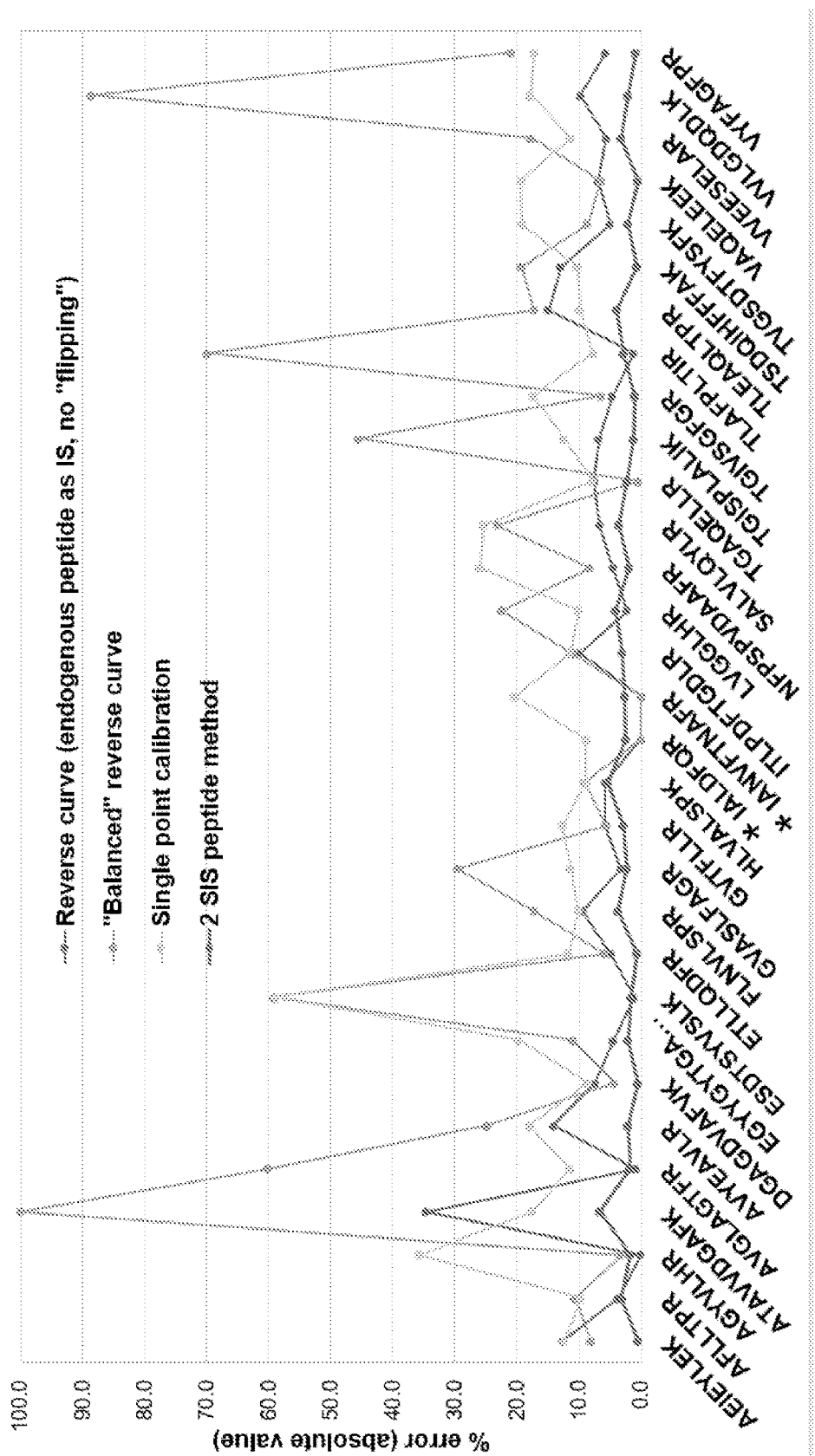
FIG. 4 is a graph showing the distribution of % error for all QC samples for double-SIS-peptide calibration system vs reverse curves and single point measurement (31 peptides, n=36; for reverse curves n=18, 3 replicates per QC level). * represents peptides without reverse curve data since no reliable endogenous signal was detected (below LLOQ).

FIG. 4 shows a graph comparing the distribution of QC sample accuracies between the different calibration strategies, shown for each peptide assayed. The double-SIS-peptide method clearly provides consistently more accurate results when compared to the reverse curve methods and single-point calibration, even when measuring the same samples prepared in the same way and at the same time. The precisions of these measurements are all similar since they are comparing the same samples on the same instrument. The difference between the methods lies in the accuracy bias that is introduced.

Example 5

Surrogate Matrix Evaluation

Another strategy that can be used to circumvent the problem of endogenous protein levels is the use of surrogate matrices to build the standard curve. This method has the advantage of needing only one SIS peptide, used as the internal standard, and the light peptide standard can be used to construct the calibration curve. The disadvantage of this approach includes the inability to prepare QC samples of known concentration prepared in human plasma. Furthermore, it can be difficult to prove the absence of matrix effects between plasma and the surrogate matrix. A common evaluation of matrix effect is the "parallelism test", where the slope of the response of SIS peptide in plasma is compared to the slope of the response in a surrogate matrix. If the slopes are identical, the matrix effects are deemed to be negligible. Establishing clear and relevant criteria for these parallelism tests can be difficult. They also often require the use of reverse curves, which do not necessarily reflect the concentration range used in the final assay.

Figure 5:
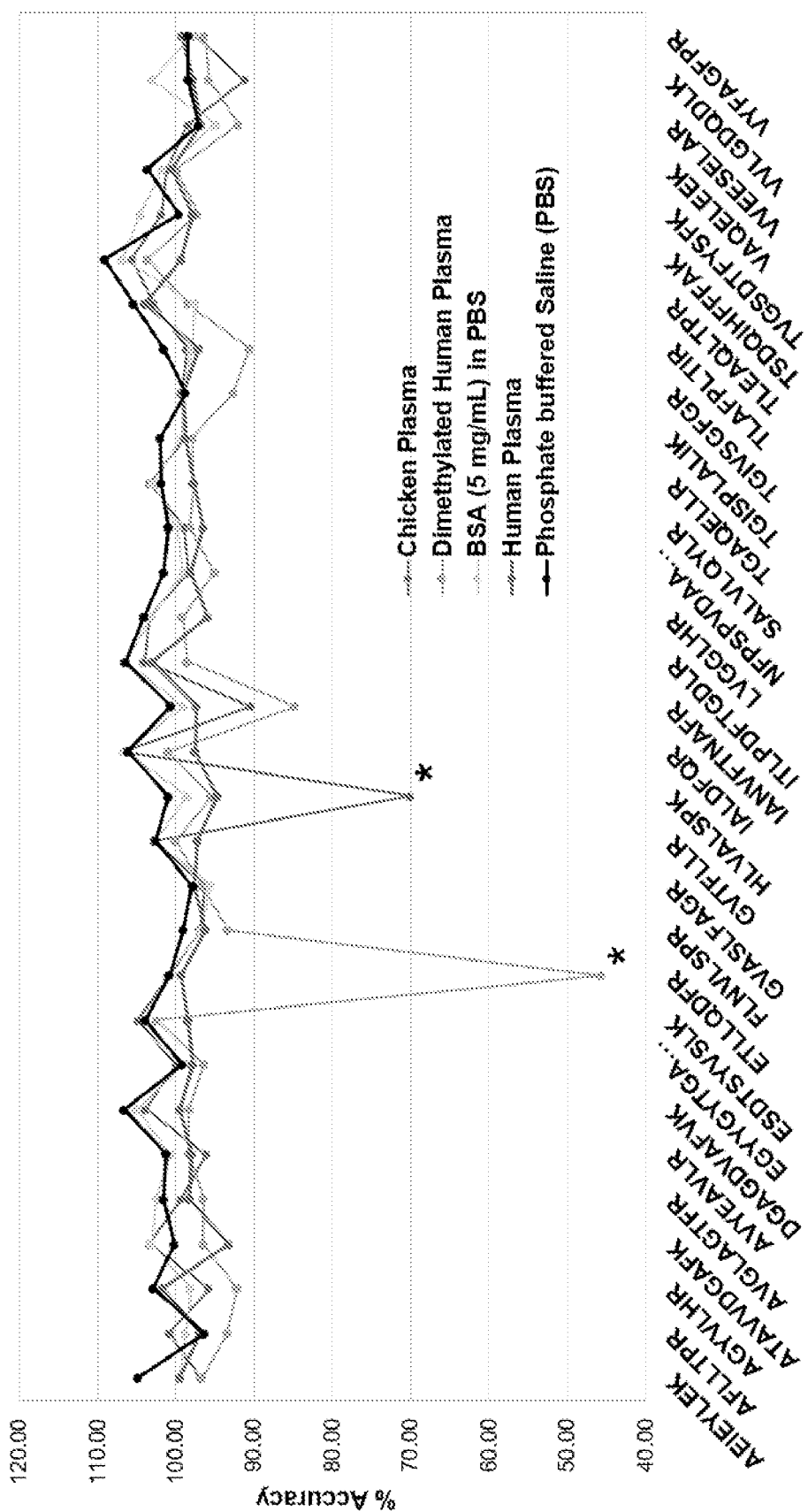
FIG. 5 is a graph showing the accuracy distribution for calibration curves prepared in different surrogate matrices (31 peptides, n=36). * represents the outlier Low QCs with a negative accuracy, due to matrix-specific interference in a single transition for a single peptide in the SIS-1 internal standard.

With the double-SIS-peptide method, surrogate matrices can be directly compared. Calibration curves were prepared in chicken plasma, dimethylated human plasma digest (where all peptides are dimethylated in order to shift the masses of all endogenous human peptides), phosphate buffered saline (PBS), and BSA solution (10 mg/ml in PBS), in addition to human plasma. The percent error calculated for the QC sample concentrations from calibration curves prepared in different matrices are shown in FIG. 5. Excellent accuracies at all QC levels, as well as similar calibration-curve slopes, were found for all of these matrices for the double SIS peptide approach.

The only examples of matrix effects for these 31 peptides were found with chicken plasma and dimethylated human plasma. The inaccuracies were a result of matrix-specific interferences present in one transition and for one peptide in each matrix. In both instances, this resulted in a low QC with negative accuracy values since the interference was present in the SIS-1 internal standards only. These particular two matrices are more complex than the others and this serves to illustrate that interferences need to be screened in both the surrogate matrix and the sample matrix when utilizing this strategy. After those transitions were discarded, the results for those peptides agreed with those obtained with the other matrices. While all the peptides tested performed well under the chosen conditions, the simpler matrices such as PBS buffer are more prone to variability due to peptide adsorption to labware during sample preparation and more care in sample handling may be required.

The ability to evaluate the accuracy of the peptide measurement using the double-SIS-peptide method can be useful, particularly during method development and validation. For example, when evaluating the LOD for a peptide in human plasma, the ability to normalize the dilution curve with a second SIS peptide improves the estimate. One advantage is when evaluating matrix effects or specificity. Instead of comparing response slopes in different matrices, one can simply prepare QC samples in different lots of plasma. The back-calculated accuracies of those samples within clear criteria will directly assess the effects of different lots of matrix at relevant concentrations within the range of the assay. Peptide recoveries can also be assessed during sample preparation, where one SIS peptides can be spiked in at different sample-preparation steps and the other SIS peptide can be spiked in prior to analysis to normalize the response.

REFERENCES (1) Percy, A. J.; Chambers, A. G.; Yang, J.; Hardie, D. B.; Borchers, C. H., Advances in multiplexed MRM-based protein biomarker quantitation toward clinical utility. *Biochim. Biophys. Acta* 2014, 1844, (5), 917-26.

(2) Baker, E. S.; Liu, T.; Petyuk, V. A.; Burnum-Johnson, K. E.; Ibrahim, Y. M.; Anderson, G. A.; Smith, R. D., Mass spectrometry for translational proteomics: progress and clinical implications. *Genome Med.* 2012, 4, (8), 63-73.

(3) Füzéry, A. K.; Levin, J.; Chan, M. M.; Chan, D. W., Translation of proteomic biomarkers into FDA approved cancer diagnostics: issues and challenges. *Clin. Prot.* 2013, 10, (1), 13-26.

(4) Sabbagh, B.; Mindt, S.; Neumaier, M.; Findeisen, P., Clinical applications of MS-based protein quantification. *Proteomics: Clin. Appl.* 2016, 10, (4), 323-45.

(5) Carr, S. A.; Abbatiello, S. E.; Ackermann, B. L.; Borchers, C.; Domon, B.; Deutsch, E. W.; Grant, R. P.; Hoofnagle, A. N.; H Uumlttenhain, R.; Koomen, J. M.; Liebler, D. C.; Liu, T.; Maclean, B.; Mani, D. R.; Mansfield, E.; Neubert, H.; Paulovich, A. G.; Reiter, L.; Vitek, O.; Aebersold, R.; Anderson, L.; Bethem, R.; Blonder, J.; Boja, E.; Botelho, J.; Boyne, M.; Bradshaw, R. A.; Burlingame, A. L.; Chan, D.; Keshishian, H.; Kuhn, E.; Kinsinger, C.; Lee, J.; Lee, S. W.; Moritz, R.; Oses-Prieto, J.; Rifai, N.; Ritchie, J.; Rodriguez, H.; Srinivas, P. R.; Townsend, R. R.; Van Eyk, J.; Whiteley, G.; Wiita, A.; Weintraub, S., Targeted Peptide Measurements in Biology and Medicine: Best Practices for Mass Spectrometry-based Assay Development Using a Fit-for-Purpose Approach. *Mol. Cell. Proteomics* 2014, 13, (3), 907-17.

(6) Campbell, J.; Rezai, T.; Prakash, A.; Krastins, B.; Dayon, L.; Ward, M.; Robinson, S.; Lopez, M., Evaluation of absolute peptide quantitation strategies using selected reaction monitoring. *Proteomics* 2011, 11, (6), 1148-52.

(7) Kruve, A.; Rebane, R.; Kipper, K.; Oldekop, M. L.; Evard, H.; Herodes, K.; Ravio, P.; Leito, I., Tutorial review on validation of liquid chromatography-mass spectrometry methods: part I. *Anal. Chim. Acta* 2015, 870, 29-44.

(8) US_Food_and_Drug_Administration, US Department of Health and Human Services, Food and Drug Administration. Guidance for Industry Bioanalytical Method Validation. http://www.fda.gov/downloads/Drugs/Guidance-ComplianceRegulatoryInformation/Guidances/ucm070107.pdf 2001.

(9) European_Medicines_Agency Guideline on bioanalytical method validation. (Feb. 13, 2017),

(10) Zhang, G.; Ueberheide, B. M.; Waldemarson, S.; Myung, S.; Molloy, K.; Eriksson, J.; Chait, B. T.; Neubert, T. A.; Fenyö, D., Protein quantitation using mass spectrometry. *Methods Mol. Biol.* 2010, 673, 211-22.

(11) Scott, K. B.; Turko, I. V.; Phinney, K. W., Quantitative performance of internal standard platforms for absolute protein quantification using multiple reaction monitoring-mass spectrometry. *Anal. Chem.* 2015, 87, (8), 4429-35.

(12) Picard, G.; Lebert, D.; Louwagie, M.; Adrait, A.; Huillet, C.; Vandenesch, F.; Bruley, C.; Garin, J.; Jaquinod, M.; Brun, V., PSAQ™ standards for accurate MS-based quantification of proteins: from the concept to biomedical applications. *J. Mass Spectrom.* 2012, 47, (10), 1353-63.

(13) Brun, V.; Dupuis, A.; Adrait, A.; Marcellin, M.; Thomas, D. D.; Court, M.; Vandenesch, F.; Garin, J., Isotope-labeled protein standards: toward absolute quantitative proteomics. *Mol. Cell. Proteomics* 2007, 6, (12), 2139-49.

(14) Scott, K. B.; Turko, I. V.; Phinney, K. W., QconCAT: Internal Standard for Protein Quantification. *Methods Enzymol.* 2016, 566, 289-303.

(15) Hoofnagle, A. N.; Whiteaker, J. R.; Carr, S. A.; Kuhn, E.; Liu, T.; Massoni, S. A.; Thomas, S. N.; Townsend, R. R.; Zimmerman, L. J.; Boja, E.; Chen, J.; Crimmins, D. L.; Davies, S. R.; Gao, Y.; Hiltke, T. R.; Ketchum, K. A.; Kinsinger, C. R.; Mesri, M.; Meyer, M. R.; Qian, W. J.; Schoenherr, R. M.; Scott, M. G.; Shi, T.; Whiteley, G. R.; Wrobel, J. A.; Wu, C.; Ackermann, B. L.; Aebersold, R.; Barnidge, D. R.; Bunk, D. M.; Clarke, N.; Fishman, J. B.; Grant, R. P.; Kusebauch, U.; Kushnir, M. M.; Lowenthal, M. S.; Moritz, R. L.; Neubert, H.; Patterson, S. D.; Rockwood, A. L.; Rogers, J.; Singh, R. J.; Van Eyk, J. E.; Wong, S. H.; Zhang, S.; Chan, D. W.; Chen, X.; Ellis, M. J.; Liebler, D. C.; Rodland, K. D.; Rodriguez, H.; Smith, R. D.; Zhang, Z.; Zhang, H.; Paulovich, A. G., Recommendations for the Generation, Quantification, Storage, and Handling of Peptides Used for Mass Spectrometry-Based Assays. *Clin. Chem.* 2016, 62, (1), 48-69.

(16) Percy, A. J.; Tamura-Wells, J.; Albar, J. P.; Aloria, K.; Amirkhani, A.; Araujo, G. D. T.; Arizmendi, J. M.; Blanco, F. J.; Canals, F.; Cho, J.-Y.; Colomé-Calls, N.; Corrales, F. J.; Domont, G.; Espadas, G.; Fernandez-Puente, P.; Gil, C.; Haynes, P. A.; Hernáez, M. L.; Kim, J. Y.; Kopylov, A.; Marcilla, M.; McKay, M. J.; Mirzaei, M.; Molloy, M. P.; Ohlund, L. B.; Paik, Y.-K.; Paradela, A.; Raftery, M.; Sabidó, E.; Sleno, L.; Wilffert, D.; Wolters, J. C.; Yoo, J. S.; Zgoda, V.; Parker, C. E.; Borchers, C. H., Inter-laboratory evaluation of instrument platforms and experimental workflows for quantitative accuracy and reproducibility assessment. *EuPA Open Proteomics* 2015, 8, 6-15.

(17) Percy, A. J.; Chambers, A. G.; Smith, D. S.; Borchers, C. H., Standardized Protocols for Quality Control of MRM-based Plasma Proteomic Workflow. *J. Proteome Res.* 2013, 12, (1), 222-33.

(18) CPTAC Assay Characterization Guidance Document. (Nov. 4, 2015),

(19) Mohammed, Y.; Bhowmick, P.; Smith, D. S.; Domanski, D.; Jackson, A. M.; Michaud, S. A.; Malchow, S.; Percy, A. J.; Chambers, A. G.; Palmer, A.; Zhang, S.; Sickmann, A.; Borchers, C. H., PeptideTracker: A knowledgebase for collecting and storing information on protein concentrations in biological tissues. *Proteomics* 2016, [Epub ahead of print].

(20) Mohammed, Y.; Domański, D.; Jackson, A. M.; Smith, D. S.; Deelder, A. M.; Palmblad, M.; Borchers, C. H., PeptidePicker: a scientific workflow with web interface for selecting appropriate peptides for targeted proteomics experiments. *J. Prot.* 2014, 106, 151-61.

(21) Kuzyk, M. A.; Parker, C. E.; Domanski, D.; Borchers, C. H., Development of MRM-based assays for the absolute quantitation of plasma proteins. *Methods Mol. Biol.* 2013, 1023, 53-82.

(22) Boersema, P. J.; Raijmakers, R.; Lemeer, S.; Mohammed, S.; Heck, A. J., Multiplex peptide stable isotope dimethyl labeling for quantitative proteomics. *Nature Protocols* 2009, 4, (4), 484-94.

(23) MacLean, B.; Tomazela, D. M.; Shulman, N.; Chambers, M.; Finney, G. L.; Frewen, B.; Kern, R.; Tabb, D. L.; Liebler, D. C.; MacCoss, M. J., Skyline: an open source document editor for creating and analyzing targeted proteomics experiments. *Bioinformatics* 2010, 26, (7), 966-8.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method of quantifying a target molecule in a test sample, comprising,
adding a first stable isotope labeled target molecule to a control sample at two or more different concentrations, wherein the control sample comprises the target molecule at an endogenous concentration of the target molecule, and wherein the control sample and test sample comprise the same matrix;
adding a second stable isotope labeled target molecule to the control sample and to the test sample in a constant concentration, wherein the label of the first and second stable isotope labeled target molecules are different such that the first stable isotope labeled target molecule and the second stable isotope labeled target molecule have distinguishable masses;
detecting an instrument signal magnitude from a mass spectrophotometer, the instrument signal magnitude measuring the first stable isotope labeled target molecule, the second stable isotope labeled target molecule, and the target molecule;
normalizing the instrument signal magnitude of the first stable isotope by generating a ratio of the instrument signal magnitude for each different concentration of the first stable isotope labeled target molecule in the control sample to the instrument signal magnitude of the second stable isotope labeled target molecule in the control sample, thereby generating a calibration curve;
normalizing the instrument signal magnitude of the target molecule by generating a ratio of the instrument signal magnitude of the target molecule in the test sample to the instrument signal magnitude of the second stable isotope labeled target molecule in the test sample; and
plotting the ratio of the instrument signal magnitude of the target molecule to the instrument signal magnitude of the second stable isotope labeled target molecule in the test sample on the calibration curve, thereby quantifying the target molecule in the test sample and avoiding matrix-specific interference.

2. The method of claim 1, wherein the test sample is biofluid, a tissue sample, a biological sample, whole blood, plasma, serum, urine, saliva, cerebral spinal fluid, tears, tumor, tissue biopsy, organ, hair, food sample, plant sample, or environmental sample.

3. The method of claim 1, wherein the first and second stable isotope labelled molecules are present in the test sample in their natural forms.

4. The method of claim 1, wherein the first and second stable isotope labelled molecules and the target molecule is a protein, peptide, small molecule, lipid, hormone, vitamin, drug, or metabolite.

5. The method of claim 1, wherein the first and second stable isotope labelled molecules and the target molecule have a mass-to-charge ratio with a positive or negative m/z range of 1 to 5000.

6. The method of claim 1, wherein the label comprises $^{2}H$, $^{13}C$, $^{15}N$, $^{18}O$, $^{34}S$, or a combination thereof.

7. The method of claim 1, wherein the first and second stable isotope labeled molecules are tryptic peptides.

8. The method of claim 1, wherein the first and/or second stable isotope labeled molecules are peptides and are labelled at valine, isoleucine, tyrosine, threonine, alanine, glutamic acid, aspartic acid, lysine or arginine.

9. A method of diagnosing, determining a risk of developing a disease, or treatment selection for disease states using the method of claim 1.

10. The method of claim 9, wherein the disease is cancer or cardiovascular disease.

11. The method of claim 1, wherein the test sample comprises a dried blood spot.

12. The method of claim 1, wherein the two or more different concentrations of the first stable isotope labeled molecule span a suspected concentration of the target molecule.

13. The method of claim 1, wherein the instrument signal magnitude is intensity, counts, or area under a curve.

14. The method of claim 1, wherein the instrument signal magnitude is an area under a curve.

15. The method of claim 1, further comprising one or more quality control samples comprising one or more concentrations of the first stable isotope labeled peptide and a constant concentration of the second stable isotope labeled peptide.

16. The method of claim 1, wherein the first and second stable isotope labeled molecules and the target molecules are enzyme digested peptides.

17. The method of claim 16, wherein the enzyme is selected from trypsin, chymotrypsin, LysN, LysC, Glu-C, Asp-N, ArgC, pepsin, proteinase K, elastase, thermolysin, papain, subtilisin, or combinations thereof.

18. A method of quantifying a target peptide in a test sample, comprising,
   adding a first stable isotope labeled target peptide to a control sample at two or more different concentrations, wherein the control sample comprises the target molecule at an endogenous concentration of the target molecule, and wherein the control sample and test sample comprise the same matrix;
   adding a second stable isotope labeled target peptide to the control sample and to the test sample in a constant concentration, wherein the label of the first and second stable isotope labeled target peptides are different such that the first stable isotope labeled peptide and the second stable isotope labeled target peptide have distinguishable masses;
   detecting a peak area by mass spectrometry of the first stable isotope labeled target peptide, the second stable isotope labeled target peptide, and the target peptide;
   normalizing the instrument signal magnitude of the first stable isotope by generating a ratio of the peak area for each different concentration of the first stable isotope labeled target peptide in the control sample to the peak area of the second stable isotope labeled target peptide in the control sample, thereby generating a calibration curve;
   normalizing the instrument signal magnitude of the first stable isotope by generating a ratio of the peak area of the target peptide in the test sample to the peak area of the second stable isotope labeled target peptide in the test sample; and
   plotting the ratio of the peak area of the target peptide to the peak area of the second stable isotope labeled target peptide in the test sample on the calibration curve, thereby quantifying the target peptide in the test sample and avoiding matrix-specific interference.

19. The method of claim 18, wherein the peptides are enzyme digested peptides.

20. The method of claim 18, wherein the test and control samples are biofluid, a tissue sample, a biological sample, whole blood, plasma, serum, urine, saliva, cerebral spinal fluid, tears, tumor, tissue biopsy, organ, hair, food sample, plant sample, or environmental sample.

\* \* \* \* \*

SEQUENCE LISTING

<160> NUMBER OF SEQ ID NOS: 32

<210> SEQ ID NO 1
<211> LENGTH: 8
<212> TYPE: PRT
<213> ORGANISM: Homo sapiens

<400> SEQUENCE: 1

Ala Glu Ile Glu Tyr Leu Glu Lys
1               5

<210> SEQ ID NO 2
<211> LENGTH: 7
<212> TYPE: PRT
<213> ORGANISM: Homo sapiens

<400> SEQUENCE: 2

Ala Phe Leu Leu Thr Pro Arg
1               5

<210> SEQ ID NO 3
<211> LENGTH: 7
<212> TYPE: PRT
<213> ORGANISM: Homo sapiens

<400> SEQUENCE: 3

Ala Gly Tyr Val Leu His Arg
1               5

<210> SEQ ID NO 4
<211> LENGTH: 10
<212> TYPE: PRT
<213> ORGANISM: Homo sapiens

<400> SEQUENCE: 4

Ala Thr Ala Val Val Asp Gly Ala Phe Lys
1               5                   10

<210> SEQ ID NO 5
<211> LENGTH: 9
<212> TYPE: PRT
<213> ORGANISM: Homo sapiens

<400> SEQUENCE: 5

Ala Val Gly Leu Ala Gly Thr Phe Arg
1               5

<210> SEQ ID NO 6
<211> LENGTH: 8
<212> TYPE: PRT
<213> ORGANISM: Homo sapiens

<400> SEQUENCE: 6

Ala Val Tyr Glu Ala Val Leu Arg
1               5

<210> SEQ ID NO 7
<211> LENGTH: 10
<212> TYPE: PRT
<213> ORGANISM: Homo sapiens

<400> SEQUENCE: 7

Asp Gly Ala Gly Asp Val Ala Phe Val Lys
1               5                   10

-continued

```
<210> SEQ ID NO 8
<211> LENGTH: 11
<212> TYPE: PRT
<213> ORGANISM: Homo sapiens

<400> SEQUENCE: 8

Glu Gly Tyr Tyr Gly Tyr Thr Gly Ala Phe Arg
1               5                   10

<210> SEQ ID NO 9
<211> LENGTH: 10
<212> TYPE: PRT
<213> ORGANISM: Homo sapiens

<400> SEQUENCE: 9

Glu Ser Asp Thr Ser Tyr Val Ser Leu Lys
1               5                   10

<210> SEQ ID NO 10
<211> LENGTH: 8
<212> TYPE: PRT
<213> ORGANISM: Homo sapiens

<400> SEQUENCE: 10

Glu Thr Leu Leu Gln Asp Phe Arg
1               5

<210> SEQ ID NO 11
<211> LENGTH: 8
<212> TYPE: PRT
<213> ORGANISM: Homo sapiens

<400> SEQUENCE: 11

Phe Leu Asn Val Leu Ser Pro Arg
1               5

<210> SEQ ID NO 12
<211> LENGTH: 9
<212> TYPE: PRT
<213> ORGANISM: Homo sapiens

<400> SEQUENCE: 12

Gly Val Ala Ser Leu Phe Ala Gly Arg
1               5

<210> SEQ ID NO 13
<211> LENGTH: 7
<212> TYPE: PRT
<213> ORGANISM: Homo sapiens

<400> SEQUENCE: 13

Gly Val Thr Phe Leu Leu Arg
1               5

<210> SEQ ID NO 14
<211> LENGTH: 8
<212> TYPE: PRT
<213> ORGANISM: Homo sapiens

<400> SEQUENCE: 14

His Leu Val Ala Leu Ser Pro Lys
1               5

<210> SEQ ID NO 15
```

<211> LENGTH: 7
<212> TYPE: PRT
<213> ORGANISM: Homo sapiens

<400> SEQUENCE: 15

Ile Ala Leu Asp Phe Gln Arg
1               5

<210> SEQ ID NO 16
<211> LENGTH: 10
<212> TYPE: PRT
<213> ORGANISM: Homo sapiens

<400> SEQUENCE: 16

Ile Ala Asn Val Phe Thr Asn Ala Phe Arg
1               5                   10

<210> SEQ ID NO 17
<211> LENGTH: 11
<212> TYPE: PRT
<213> ORGANISM: Homo sapiens

<400> SEQUENCE: 17

Ile Thr Leu Pro Asp Phe Thr Gly Asp Leu Arg
1               5                   10

<210> SEQ ID NO 18
<211> LENGTH: 7
<212> TYPE: PRT
<213> ORGANISM: Homo sapiens

<400> SEQUENCE: 18

Leu Val Gly Gly Leu His Arg
1               5

<210> SEQ ID NO 19
<211> LENGTH: 11
<212> TYPE: PRT
<213> ORGANISM: Homo sapiens

<400> SEQUENCE: 19

Asn Phe Pro Ser Pro Val Asp Ala Ala Phe Arg
1               5                   10

<210> SEQ ID NO 20
<211> LENGTH: 9
<212> TYPE: PRT
<213> ORGANISM: Homo sapiens

<400> SEQUENCE: 20

Ser Ala Leu Val Leu Gln Tyr Leu Arg
1               5

<210> SEQ ID NO 21
<211> LENGTH: 8
<212> TYPE: PRT
<213> ORGANISM: Homo sapiens

<400> SEQUENCE: 21

Thr Gly Ala Gln Glu Leu Leu Arg
1               5

<210> SEQ ID NO 22
<211> LENGTH: 10
<212> TYPE: PRT

```
<213> ORGANISM: Homo sapiens

<400> SEQUENCE: 22

Thr Gly Ile Ser Pro Leu Ala Leu Ile Lys
1               5                   10

<210> SEQ ID NO 23
<211> LENGTH: 9
<212> TYPE: PRT
<213> ORGANISM: Homo sapiens

<400> SEQUENCE: 23

Thr Gly Ile Val Ser Gly Phe Gly Arg
1               5

<210> SEQ ID NO 24
<211> LENGTH: 9
<212> TYPE: PRT
<213> ORGANISM: Homo sapiens

<400> SEQUENCE: 24

Thr Leu Ala Phe Pro Leu Thr Ile Arg
1               5

<210> SEQ ID NO 25
<211> LENGTH: 9
<212> TYPE: PRT
<213> ORGANISM: Homo sapiens

<400> SEQUENCE: 25

Thr Leu Glu Ala Gln Leu Thr Pro Arg
1               5

<210> SEQ ID NO 26
<211> LENGTH: 11
<212> TYPE: PRT
<213> ORGANISM: Homo sapiens

<400> SEQUENCE: 26

Thr Ser Asp Gln Ile His Phe Phe Phe Ala Lys
1               5                   10

<210> SEQ ID NO 27
<211> LENGTH: 11
<212> TYPE: PRT
<213> ORGANISM: Homo sapiens

<400> SEQUENCE: 27

Thr Val Gly Ser Asp Thr Phe Tyr Ser Phe Lys
1               5                   10

<210> SEQ ID NO 28
<211> LENGTH: 8
<212> TYPE: PRT
<213> ORGANISM: Homo sapiens

<400> SEQUENCE: 28

Val Ala Gln Glu Leu Glu Glu Lys
1               5

<210> SEQ ID NO 29
<211> LENGTH: 9
<212> TYPE: PRT
<213> ORGANISM: Homo sapiens
```

```
<400> SEQUENCE: 29

Val Val Glu Glu Ser Glu Leu Ala Arg
1               5

<210> SEQ ID NO 30
<211> LENGTH: 9
<212> TYPE: PRT
<213> ORGANISM: Homo sapiens

<400> SEQUENCE: 30

Val Val Leu Gly Asp Gln Asp Leu Lys
1               5

<210> SEQ ID NO 31
<211> LENGTH: 8
<212> TYPE: PRT
<213> ORGANISM: Homo sapiens

<400> SEQUENCE: 31

Val Tyr Phe Ala Gly Phe Pro Arg
1               5

<210> SEQ ID NO 32
<211> LENGTH: 19
<212> TYPE: PRT
<213> ORGANISM: Homo sapiens

<400> SEQUENCE: 32

Ser Ser Pro Val Val Ile Asp Ala Ser Thr Ala Ile Asp Ala Pro Ser
1               5                   10                  15

Asn Leu Arg
```